(12) United States Patent
Kara et al.

(10) Patent No.: US 11,098,335 B2
(45) Date of Patent: Aug. 24, 2021

(54) EXPRESSION SYSTEM

(71) Applicant: Fujifilm Diosynth Biotechnologies UK Limited, Billingham (GB)

(72) Inventors: Bhupendra Vallabh Kara, Billingham (GB); Christopher David John Lennon, Billingham (GB); Ian John Hodgson, Billingham (GB)

(73) Assignee: Fujifilm Diosynth Biotechnologies UK Limited, Billingham (GB)

( * ) Notice: Subject to any disclaimer, the term of this patent is extended or adjusted under 35 U.S.C. 154(b) by 0 days.

(21) Appl. No.: 15/588,851

(22) Filed: May 8, 2017

(65) Prior Publication Data

US 2017/0240943 A1    Aug. 24, 2017

Related U.S. Application Data

(63) Continuation of application No. 13/966,600, filed on Aug. 14, 2013, now Pat. No. 9,677,103, which is a continuation of application No. 12/223,527, filed as application No. PCT/GB2007/000351 on Feb. 1, 2007, now Pat. No. 8,530,188.

(30) Foreign Application Priority Data

Feb. 3, 2006    (GB) ...................................... 0602173

(51) Int. Cl.
| | |
|---|---|
| C12P 21/00 | (2006.01) |
| C12N 15/70 | (2006.01) |
| C12N 15/72 | (2006.01) |
| C12N 15/73 | (2006.01) |
| C12R 1/19 | (2006.01) |
| C12N 15/78 | (2006.01) |
| C12N 15/81 | (2006.01) |
| C12N 15/85 | (2006.01) |

(52) U.S. Cl.
CPC .............. *C12P 21/00* (2013.01); *C12N 15/70* (2013.01); *C12N 15/72* (2013.01); *C12N 15/73* (2013.01); *C12N 15/78* (2013.01); *C12N 15/81* (2013.01); *C12N 15/85* (2013.01); *C12R 1/19* (2013.01)

(58) Field of Classification Search
CPC ................................ C12N 15/73; C12N 15/72
See application file for complete search history.

(56) References Cited

U.S. PATENT DOCUMENTS

| | | | | |
|---|---|---|---|---|
| 5,059,530 A | * | 10/1991 | Oshima ................ | C07K 14/525 |
| | | | | 435/252.33 |
| 5,416,014 A | | 5/1995 | Burtscher et al. | |
| 5,589,392 A | | 12/1996 | Short | |
| 5,840,521 A | * | 11/1998 | Barth .................... | C07K 14/415 |
| | | | | 435/69.1 |
| 6,355,775 B1 | | 3/2002 | Nagasawa et al. | |
| 6,537,779 B1 | * | 3/2003 | Kara .................... | C12N 15/72 |
| | | | | 435/252.3 |
| 2005/0186666 A1 | | 8/2005 | Schneider et al. | |
| 2006/0251670 A1 | * | 11/2006 | Comanducci ........ | A61K 39/095 |
| | | | | 424/190.1 |
| 2009/0325230 A1 | | 12/2009 | Schneider et al. | |

FOREIGN PATENT DOCUMENTS

| | | |
|---|---|---|
| EP | 0357391 A2 | 3/1990 |
| EP | 0502637 A2 | 9/1992 |
| JP | 63-267288 A | 4/1988 |
| WO | 1991/13979 A1 | 9/1991 |
| WO | 1993/15769 A1 | 8/1993 |
| WO | 1998/22578 A1 | 5/1998 |
| WO | 1999/05279 A1 | 2/1999 |
| WO | 2002/086098 A2 | 10/2002 |
| WO | 2002/099100 A2 | 12/2002 |
| WO | 2004/056964 A2 | 7/2004 |
| WO | 2005/058946 A2 | 6/2005 |
| WO | 2005/071089 A2 | 8/2005 |
| WO | 2008/020650 A1 | 2/2008 |
| WO | 2008/051854 A2 | 5/2008 |

OTHER PUBLICATIONS

Cheng et al., Nucl. Acids. Res. 20 (17): 4591-4598 (Year: 1992).*
Baneyx, Curr. Opin. Biotechn., 10:411-421, 1999 (Year: 1999).*
Brunner et al. (1987) Promoter recognition and promoter strength in the *Escherichia coli* system. The EMBO Journal, 6(10):3139-3144 (Year: 1987).*
Lutz et al. (1997) Independent and tight regulation of transcriptional units in Escherichia coli via the LacR/O, the TetR/O and AraC/I1-I2 regulatory elements. Nucleic acid Research, 25(6):1203-1210 (Year: 1997).*
Becker et al., "Bacterial repression loops require enhanced DNA flexibility," Journal of Molecular Biology, 349: 716-730 (2005).
Brosius et al., "Regulation of ribosomal RNA promoters with a synthetic lac operator," Proceedings of the National Academy of Sciences, 81: 6929-6933 (1984).
Brosius et al., "Spacing of the -10 and -35 Regions in the tac Promoter," Journal of Biological Chemistry, 260: 3539-3541 (1985).
Dubendorff et al., "Controlling Basal Expression in an Inducible T7 Expression System by Blocking the Target T7 Promoter with lac Repressor," Journal of Molecular Biology, 219: 45-59 (1991).
Edamatsu et al., "Inducible high-level expression vector for mammalian cells, pEF-Lac carrying human elongation factor 1α promoter and lac operator," Gene, 187: 289-294 (1997).
Flashner et al., "Dual mechanism of repression at a distance in the lac operon," Proceedings of the National Academy of Sciences, 85: 8968-8972 (1988).

(Continued)

*Primary Examiner* — Neil P Hammell
(74) *Attorney, Agent, or Firm* — Morgan, Lewis & Bockius LLP

(57) ABSTRACT

A perfect palindrome operator sequence-based protein expression system is provided. The expression system comprises a promoter; and a perfect palindrome operator sequence, wherein the promoter is not T7. The expression system is preferably employed for the production of recombinant proteins by fermentation.

9 Claims, 16 Drawing Sheets

Specification includes a Sequence Listing.

(56) References Cited

OTHER PUBLICATIONS

Lanzer et al., "Promoters largely determine the efficiency of repressor action," Proceedings of the National Academy of Sciences, 85: 8973-8977 (1988).
Oehler et al., "Quality and position of the three lac operators of *E.coli* define efficiency of repression," EMBO Journal, 13: 3348-3355 (1994).
Sadler et al., "A perfectly symmetric lac operator binds the lac repressor very tightly," Proceedings of the National Academy of Sciences, 80: 6785-6789 (1983).
Sagawa et al., "A tightly regulated expression system in *Escherichia coli* with SP6 RNA polymerase," Gene, 168: 37-41 1996).
Savochkina et al., "Stability of Cloned Promoter-Containing Fragments," Molecular & General Genetics, 189: 142-147 (1983).
Simons et al., "Possible ideal lac operator: *Escherichia coli* lac operator-like sequences from eukaryotic genomes lack the central G-C pair," Proceedings of the National Academy of Sciences, 81: 1624-1628 (1984).
Srivastava et al., "Gene expression systems in corynebacteria," Protein Expression and Purification, 40: 221-229 (2005).
Studier et al., "Use of Bacteriophage T7 RNA Polymerase to Direct Selective High-level Expression of Cloned Genes," Journal of Molecular Biology, 189: 113-130 (1986).
Dandanell et al., "Two operator sites separated by 599 base pairs are required for deoR repression of the deo operon of *Escherichia coli*," EMBO Journal, 4: 3333-3338 (1985).

\* cited by examiner

Figure 1

D1.3 Sequence (SEQ ID NO 17)

CATATGAAATACCTATTGCCTACGGCAGCCGCTGGATTGTTATTACTCGCTGCCCAA
CCAGCGATGGCCCAGGTGCAGCTGCAGGAGTCAGGACCTGGCCTGGTGGCGCCCT
CACAGAGCCTGTCCATCACATGCACCGTCTCAGGGTTCTCATTAACCGGCTATGGTG
TAAACTGGGTTCGCCAGCCTCCAGGAAAGGGTCTGGAGTGGCTGGGAATGATTTGG
GGTGATGGAAACACAGACTATAATTCAGCTCTCAAATCCAGACTGAGCATCAGCAAG
GACAACTCCAAGAGCCAAGTTTTCTTAAAAATGAACAGTCTGCACACTGATGACACAG
CCAGGTACTACTGTGCCAGAGAGAGAGATTATAGGCTTGACTACTGGGGCCAAGGG
ACCACGGTCACCGTCTCCTCAGCCTCCACCAAGGGCCCATCGGTCTTCCCCCTGGC
ACCCTCCTCCAAGAGCACCTCTGGGGGCACAGCGGCCCTGGGCTGCCTGGTCAAG
GACTACTTCCCCGAACCGGTGACGGTGTCGTGGAACTCAGGCGCCCTGACCAGCGG
CGTGCACACCTTCCCGGCTGTCCTACAGTCCTCAGGACTCTACTCCCTCAGCAGCGT
GGTGACTGTGCCCTCCAGTAGCTTGGGCACCCAGACCTACATCTGCAACGTGAATCA
CAACCCCAGCAACACCAAGGTCGACAAGAAAGTTGAGCCCAAATCTTCAACTAAGAC
GCACACATCAGGAGGTGAACAGAAGCTCATCTCAGAAGAGGATCGAATTAATAAGG
GAGCTTGCATGCAAATTCTATTTCAAGGAGACAGTCATAATGAAATACCTATTGCCTA
CGGCAGCCGCTGGATTGTTATTACTCGCTGCCCAACCAGCGATGGCCGACATCGAG
CTCACCCAGTCTCCAGCCTCCCTTTCTGCGTCTGTGGGAGAAACTGTCACCATCACA
TGTCGAGCAAGTGGGAATATTCACAATTATTTAGCATGGTATCAGCAGAAACAGGGA
AAATCTCCTCAGCTCCTGGTCTATTATACAACAACCTTAGCAGATGGTGTGCCATCAA
GGTTCAGTGGCAGTGGATCAGGAACACAATATTCTCTCAAGATCAACAGCCTGCAAC
CTGAAGCTTTTGGGAGTTATTACTGTCAACATTTTTGGAGTACTCCTCGGACGTTCGG
TGGAGGGACCAAGCTCGAGATCAAACGGACTGTGGCTGCACCATCTGTCTTCATCTT
CCCGCCATCTGATGAGCAGTTGAAATCTGGAACTGCCTCTGTTGTGCCTGCTGAA
TAACTTCTATCCCAGAGAGGCCAAAGTACAGTGGAAGGTGGATAACGCCCTCCAATC
GGGTAACTCCCAGGAGAGTGTCACAGAGCAGGACAGCAAGGACAGCACCTACAGCC
TCAGCAGCACCCTGACGCTGAGCAAAGCAGACTACGAGAAACACAAAGTCTACGCC
TGCGAAGTCACCCATCAGGGCCTGAGTTCGCCCGTCACAAAGAGCTTCAACCGCGG
AGAGTCATAGTAAGGATCC (*) = Basal expression, no inducer (IPTG) added
(**) = % TCP, % Total Cell Protein Arrow denotes hTNFα band Lane 6: CLD038: 2h incubation (pre-induction)
Lane 5: CLD038: 4h incubation (pre-induction)
Lane 4: CLD038: 1h post IPTG induction
Lane 3: CLD038: 2h post IPTG induction
Lane 2: CLD038: 3h post IPTG induction
Lane 1: CLD038: 4h post IPTG induction
Lane 7: Molecular weight markers

Figure 5

D1.3-A5B7 Bispecific Single Chain Tetravalent Diabody (bsctDb) Sequence (SEQ ID NO 22)

CATATGAAAAAGACAGCTATCGCGATTGCAGTGGCACTGGCTGGTTTCGCTACCGTA
GCTCAAGCCCAGGTGCAGCTGCAGGAGTCAGGACCTGGCCTGGTGGCGCCCTCAC
AGAGCCTGTCCATCACATGCACCGTCTCAGGGTTCTCATTAACCGGCTATGGTGTAA
ACTGGGTTCGCCAGCCTCCAGGAAAGGGTCTGGAGTGGCTGGGAATGATTTGGGGT
GATGGAAACACAGACTATAATTCAGCTCTCAAATCCAGACTGAGCATCAGCAAGGAC
AACTCCAAGAGCCAAGTTTTCTTAAAAATGAACAGTCTGCACACTGATGACACAGCCA
GGTACTACTGTGCCAGAGAGAGAGATTATAGGCTTGACTACTGGGGCCAAGGGACC
ACGGTCACCGTCTCCTCAGCCTCCACCAAGGGCCCATCGAGCGCCAAAACCACCCC
GGACATCGAGCTCTCCCAGTCTCCAGCAATCCTGTCTGCATCTCCAGGGGAGAAGG
TCACAATGACTTGCAGGGCCAGCTCAAGTGTAACTTACATTCACTGGTACCAGCAGA
AGCCAGGATCCTCCCCAAATCCTGGATTTATGCCACATCCAACCTGGCTTCTGGAG
TCCCTGCTCGCTTCAGTGGCAGTGGGTCTGGGACCTCTTACTCTCTCACAATCAGCA
GAGTGGAGGCTGAAGATGCTGCCACTTATTACTGCCAACATTGGAGTAGTAAACCAC
CGACGTTCGGTGGAGGCACCAAGCTCGAGATCAAACGGACTGTGCGCGCCGATGC
CGCCCCGACCGTGCAGGTGCAGCTGCAGGAATCTGGTGGTGGCTTAGTTCAACCTG
GTGGTTCCCTGAGACTCTCCTGTGCAACTTCTGGGTTCACCTTCACTGATTACTACAT
GAACTGGGTCCGCCAGCCTCCAGGAAAGGCACTTGAGTGGTTGGGTTTTATTGGAA
ACAAAGCTAATGGTTACACAACAGAGTACAGTGCATCTGTGAAGGGTCGGTTCACCA
TCTCCAGAGATAAATCCCAAAGCATCCTCTATCTTCAAATGAACACCCTGAGAGCTGA
GGACAGTGCCACTTATTACTGTACAAGAGATAGGGGGCTACGGTTCTACTTTGACTA
CTGGGGCCAAGGCACCACGGTCACCGTCTCCTCAGCCTCCACCAAGGGCCCATCGA
GCGCCAAAACCACCCCGGACATCGAGCTCACCCAGTCTCCAGCCTCCCTTTCTGCG
TCTGTGGGAGAAACTGTCACCATCACATGTCGAGCAAGTGGGAATATTCACAATTATT
TAGCATGGTATCAGCAGAAACAGGGAAAATCTCCTCAGCTCCTGGTCTATTATACAAC
AACCTTAGCAGATGGTGTGCCATCAAGGTTCAGTGGCAGTGGATCAGGAACACAATA
TTCTCTCAAGATCAACAGCCTGCAACCTGAAGCTTTTGGGAGTTATTACTGTCAACAT
TTTTGGAGTACTCCTCGGACGTTCGGTGGAGGGACCAAGCTCGAGATCAAACGGAC
TGTGGGATCCGAACAAAAGCTGATCTCAGAAGAAGACCTAAACTCATGATAAGCGGC
CGC

Figure 6

GST-3C Fusion Sequence (SEQ ID NO 23)

CATATGTCCCCTATACTAGGTTATTGGAAAATTAAGGGCCTTGTGCAACCCACTCGAC
TTCTTTTGGAATATCTTGAAGAAAAATATGAAGAGCATTTGTATGAGCGCGATGAAGG
TGATAAATGGCGAAACAAAAAGTTTGAATTGGGTTTGGAGTTTCCCAATCTTCCTTAT
TATATTGATGGTGATGTTAAATTAACACAGTCTATGGCCATCATACGTTATATAGCTGA
CAAGCACAACATGTTGGGTGGTTGTCCAAAAGAGCGTGCAGAGATTTCAATGCTTGA
AGGAGCGGTTTTGGATATTAGATACGGTGTTTCGAGAATTGCATATAGTAAAGACTTT
GAAACTCTCAAAGTTGATTTTCTTAGCAAGCACCTGAAATGCTGAAAATGTTCGAAG
ATCGTTTATGTCATAAAACATATTTAAATGGTGATCATGTAACCCATCCTGACTTCATG
TTGTATGACGCTCTTGATGTTGTTTTATACATGGACCCAATGTGCCTGGATGCGTTCC
CAAAATTAGTTTGTTTTAAAAAACGTATTGAAGCTATCCCACAAATTGATAAGTACTTG
AAATCCAGCAAGTATATAGCATGGCCTTTGCAGGGCTGGCAAGCCACGTTTGGTGGT
GGCGACCATCCTCCAAAATCGGATCTGGTTCCGCGTGGATCCGGACCAAACACAGA
ATTTGCACTATCCCTGTTAAGGAAAAACATAATGACTATAACAACCTCAAAGGGAGAG
TTCACAGGGTTAGGCATACATGATCGTGTCTGTGTGATACCCACACACGCACAGCCT
GGTGATGATGTACTAGTGAATGGTCAGAAAATTAGAGTTAAGGATAAGTACAAATTAG
TAGATCCAGAGAACATTAATCTAGAGCTTACAGTGTTGACTTTAGATAGAAATGAAAA
ATTCAGAGATATCAGGGGATTTATATCAGAAGATCTAGAAGGTGTGGATGCCACTTTG
GTAGTACATTCAAATAACTTTACCAACACTATCTTAGAAGTTGGCCCTGTAACAATGG
CAGGACTTATTAATTTGAGTAGCACCCCACTAACAGAATGATTCGTTATGATTATGC
AACAAAAACTGGGCAGTGTGGAGGTGTGCTGTGTGCTACTGGTAAGATCTTTGGTAT
TCATGTTGGCGGTAATGGAAGACAAGGATTTTCAGCTCAACTTAAAAAACAATATTTT
GTAGAGAAACAATAAGAATTCC

Figure 7

Interferon α2 Sequence (SEQ ID NO 24)

CATATGATGTGTGATCTGCCGCAAACTCATAGCCTGGGTAGCCGTCGCACCCTGATG
CTGCTGGCCCAAATGCGCCGTATCTCCCTGTTCTCCTGTCTGAAAGACCGCCATGAC
TTTGGCTTCCCGCAGGAAGAGTTCGGTAACCAGTTCCAAAAGGCAGAAACTATCCCG
GTACTGCACGAAATGATTCAACAGATTTTTAACCTGTTCAGCACTAAAGACTCCTCT
GCTGCATGGGACGAAACTCTCCTGGACAAATTCTACACCGAACTGTACCAGCAACTG
AACGACCTGGAAGCCTGCGTCATCCAGGGTGTTGGCGTAACCGAAACTCCGCTGAT
GAAAGAAGACTCCATCCTGGCTGTTCGCAAATACTTCCAGCGTATCACCCTGTACCT
GAAAGAGAAGAAATACAGCCCGTGCGCTTGGGAAGTTGTACGCGCTGAAATCATGC
GTTCCTTCAGCCTGTCCACTAACCTGCAAGAATCTCTGCGTAGCAAAGAATAACTCG
AG

Figure 8

Erythropoietin (EPO) Sequence (SEQ ID NO 25)

CATATGGCTCCGCCACGTCTGATTTGTGACTCTCGCGTTCTGGAGCGTTACCTGCTG
GAGGCCAAGGAAGCCGAAAACATCACGACCGGTTGTGCGGAACATTGCTCTCTGAA
TGAGAACATCACTGTTCCGGATACGAAGGTTAACTTCTACGCTTGGAAACGTATGGA
AGTAGGCCAGCAGGCAGTAGAAGTGTGGCAGGGTCTGGCGCTGCTGTCCGAAGCG
GTTCTGCGTGGCCAGGCGCTGCTGGTCAACTCCAGCCAGCCGTGGGAGCCGCTGC
AGCTGCACGTAGATAAAGCGGTTAGCGGTCTGCGTTCCCTGACTACCCTGCTGCGC
GCGCTGGGTGCGCAAAAGAAGCTATCTCCCCGCCAGATGCGGCATCTGCAGCCCC
GCTGCGTACCATCACTGCAGATACTTTCCGCAAGCTGTTTCGTGTTTATTCCAACTTC
CTGCGTGGTAAACTGAAGCTGTACACCGGTGAAGCGTGCCGTACCGGCGATCGTTA
ATAAACTCGAG

Figure 9

L-2-Haloalkanoate Dehalogenase (hadL) Sequence (SEQ ID NO 26)

CATATGAAGGAAATAACCAATGAAAAACATCCAAGGTATCGTTTTCGATTTGTATGGC
ACGCTCTACGACGTGCATTCCGTGGTGCAAGCCTGTGAAGAGGTCTATCCGGGCCA
AGGCGACGCTATTTCTCGCCTCTGGCGGCAAAAGCAATTGGAATACACCTGGCTCAG
GAGCCTCATGGGCCGTTACGTGAACTTTGAGAAAGCAACAGAGGATGCCTTGCGCTT
TACCTGCACGCATCTGGGCTTGTCGCTCGATGATGAAACCCACCAGCGCCTCAGTG
ATGCTTATTTGCACCTCACCCCTTATGCCGATACAGCTGACGCCGTTCGCCGTTTGA
AAGCTGCGGGCCTACCGCTAGGCATCATTTCAAATGGTTCTCATTGCTCGATCGAGC
AAGTCGTGACTAACTCTGAAATGAATTGGGCGTTCGATCAGCTGATCAGCGTCGAGG
ATGTGCAAGTGTTCAAACCTGATAGTCGCGTCTATAGCCTTGCCGAGAAGCGCATGG
GTTTTCCAAAGGAAAACATCCTCTTCGTTTCGTCAAACGCGTGGGATGCGAGTGCAG
CCAGTAACTTTGGTTTCCCGGTTTGCTGGATCAATCGGCAGAACGGCGCGTTTGATG
AGCTGGATGCAAAGCCGACACACGTCGTGCGTAATCTCGCCGAAATGTCGAACTGG
CTGGTTAATTCGCTCGATTAATGAAGGATCC

Arrow denotes position for HadL protein

Lane 1: Molecular weight markers
Lane 2: Flask 1 - CLD075 pre-induction
Lane 3: Flask 2 - CLC075 pre-induction
Lane 4: Flask 1 - CLD075, 6h culture, 3h post 0.5mM IPTG induction
Lane 5: Flask 2 - CLD075, 6h culture, no induction
Lane 6: Flask 1 - CLD075, 23h culture, 20h post 0.5mM IPTG induction
Lane 7: Flask 2 - CLD075, 23h culture, no induction
Lane 8: Molecular weight markers

Figure 11

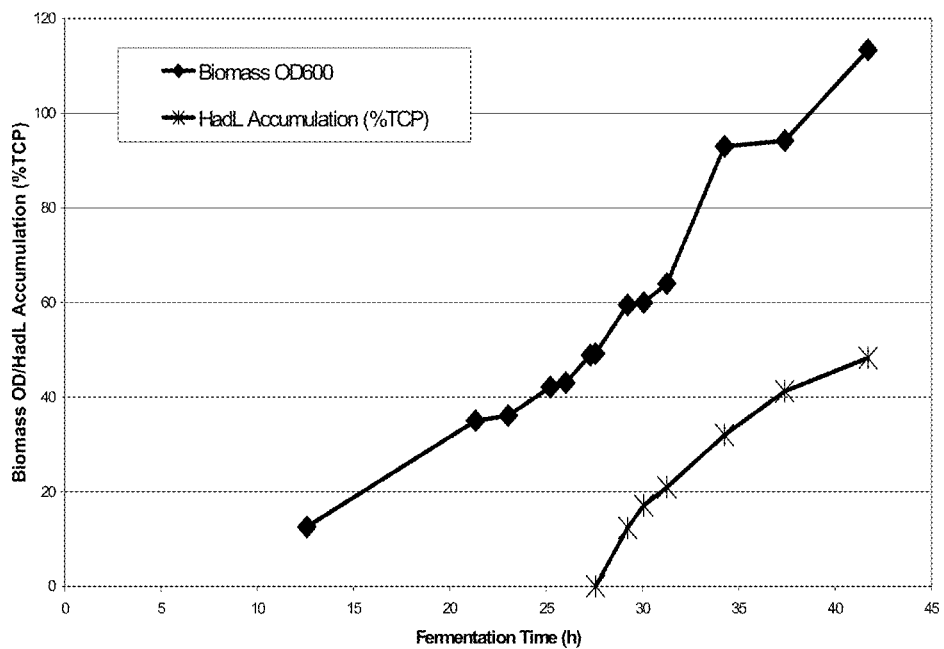

Figure 12 hCMV Promoter and Lac Operator Sequence (SEQ ID NO 33)

CATATGCCAAGTCCGCCCCCTATTGACGTCAATGACGGTAAATGGCCCGCCTGGCAT
TATGCCCAGTACATGACCTTACGGGACTTTCCTACTTGGCAGTACATCTACGTATTAG
TCATCGCTATTATACCATGGTGATGCGGTTTTGGCAGTACACCAATGGGCGTGGATA
GCGGTTTGACTCACGGGGATTTCCAAGTCTCCACCCCATTGACGTCAATGGGAGTTT
GTTTTGGCACCAAAATCAACGGGACTTTCCAAAATGTCGTAATAACCCCGCCCCGTT
GACGCAAATGGGGAATTGTGAGCGCTCACAATTCCTCTATATAAGCAGAGCTCGTTT
AGTGAACCGTCAGATCACTAGATGCGTACAGTCCGATGACTTGCATGGAATTGTGAG
CGCTCACAATTCCAAGCTTTATTGCGGTATAGGCTAGC

Figure 13

IgG Fc Sequence (SEQ ID NO 34)

ATGGAGACAGACACACTCCTGCTATGGGTACTGCTGCTCTGGGTTCCAGGTTCCACT
GGTGACGCGGCCCAGCCGGCCAGGCGCGCGCGCCGTACGTACAAGCTTGGATCCG
CAGAGCCCAAATCTTGTGACAAAACTCACACATGCCCACCGTGCCCAGCACCTGAAC
TCCTGGGGGGACCGTCAGTCTTCCTCTTCCCCCCAAAACCCAAGGACACCCTCATGA
TCTCCCGGACCCCTGAGGTCACATGCGTGGTGGTGGACGTGAGCCACGAAGACCCT
GAGGTCAAGTTCAACTGGTACGTGGACGGCGTGGAGGTGCATAATGCCAAGACAAA
GCCGCGGGAGGAGCAGTACAACAGCACGTACCGTGTGGTCAGCGTCCTCACCGTC
CTGCACCAGGACTGGCTGAATGGCAAGGAGTACAAGTGCAAGGTCTCCAACAAAGC
CCTCCCAGCCCCCATCGAGAAAACCATCTCCAAAGCCAAAGGGCAGCCCCGAGAAC
CACAGGTGTACACCCTGCCCCCATCCCGGGATGAGCTGACCAAGAACCAGGTCAGC
CTGACCTGCCTGGTCAAAGGCTTCTATCCCAGCGACATCGCCGTGGAGTGGGAGAG
CAATGGGCAGCCGGAGAACAACTACAAGACCACGCCTCCCGTGCTGGACTCCGACG
GCTCCTTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGCAGAAG
AGCCTCTCCCTGTCTCCGGGTAAATGA (For both induced and un-induced n=4. Data presented are mean with error bars representing 1 standard deviation)

Figure 15

Clone Sequence 1 used in Example 20 (SEQ ID NO 35)

CTCGAGGCATGTGCTCTGTATGTATATAAAACTCTTGTTTTCTTCTTTTCTCTAAATATT
CTTTCCTTATACATTAGGACCTTTGCAGCATAAATTACTATACTTCTATAGACACGCAA
ACACAAATACACACACTAAATGGCGGAGCTGAATTACATTCCCAACCGCGTGGCACA
ACAACTGGCGGGCAAACAGTCGTTGCTGATTGGCGTTGCCACCTCCAGTCTGGCCC
TGCACGCGCCGTCGCAAATTGTCGCGGCGATTAAATCTCGCGCCGATCAACTGGGT
GCCAGCGTGGTGGTGTCGATGGTAGAACGAAGCGGCGTCGAAGCCTGTAAAGCGG
CGGTGCACAATCTTCTCGCGCAACGCGTCAGTGGGCTGATCATTAACTATCCGCTGG
ATGACCAGGATGCCATTGCTGTGGAAGCTGCCTGCACTAATGTTCCGGCGTTATTTC
TTGATGTCTCTGACCAGACACCCATCAACAGTATTATTTTCTCCCATGAAGACGGTAC
GCGACTGGGCGTGGAGCATCTGGTCGCATTGGGTCACCAGCAAATCGCGCTGTTAG
CGGGCCCATTAAGTTCTGTCTCGGCGCGTCTGCGTCTGGCTGGCTGGCATAAATATC
TCACTCGCAATCAAATTCAGCCGATAGCGGAACGGGAAGGCGACTGGAGTGCCATG
TCCGGTTTTCAACAAACCATGCAAATGCTGAATGAGGGCATCGTTCCCACTGCGATG
CTGGTTGCCAACGATCAGATGGCGCTGGGCGCAATGCGCGCCATTACCGAGTCCGG
GCTGCGCGTTGGTGCGGATATCTCGGTAGTGGGATACGACGATACCGAAGACAGCT
CATGTTATATCCCGCCGTTAACCACCATCAAACAGGATTTTCGCCTGCTGGGGCAAA
CCAGCGTGGACCGCTTGCTGCAACTCTCTCAGGGCCAGGCGGTGAAGGGCAATCAG
CTTTTGCCCGTCTCACTGGTGAAAAGAAAAACCACCCTGGCGCCCAATACGCAAACC
GCCTCTCCCCGCGCGTTGGCCGATTCATTAATGCAGCTCGCACGACAGGTTTCCCG
ACTGGAAAGCGGGCAGTGACTCGAG

Figure 16

Clone Sequence 2 used in Example 20 (SEQ ID NO 36)

GGATCCTAGGCAATAATTATGAGATAAATGGTGCAGCACTATTAAGTAGTGTGGATTT
CAATAATTTCCGAATTAGGAATAAATGCGCTAAATAGACATCCCGTTCTCTTTGGTAAT
CTGCATAATTCTGATGCAATATCCAACAACTATTTGTGCAATTATTTAACAAAATCCAA
TTAACTTTCCTAATTAGTCCTTCAATAGAACATCTGTATTCCTTTTTTTATGAACACCT
TCCTAATTAGGCCATCAACGACAGTAAATTTTGCCGAATTTAATAGCTTCTACTGAAAA
ACAGTGGACCATGTGAAAAGATGCATCTCATTTATCAAACACATAATATTCAAGTGAG
CCTTACTTCAATTGTATTGAAGTGCAAGAAAACCAAAAAGCAACAACAGGTTTTGGAT
AAGTACATATATAAGGGAATTGTGAGCGCTCACAATTCCTGTTACTGTTCTTACGATT
CATTTACGATTCAAGAATAGTTCAAACAAGAAGATTACAAACTATCAATGGAATTGTGA
GCGCTCACAATTCCAAGAATGAGATTTCCTTCAATTTTTACTGCTGTTTTATTCGCAGC
ATCCTCCGCATTAGCTGCTCCAGTCAACACTACAACAGAAGATGAAACGGCACAAAT
TCCGGCTGAAGCTGTCATCGGTTACTCAGATTTAGAAGGGGATTTCGATGTTGCTGT
TTTGCCATTTTCCAACAGCACAAATAACGGGTTATTGTTTATAAATACTACTATTGCCA
GCATTGCTGCTAAAGAAGAAGGGGTATCTCTCGAGAAAAGAGAGGCTGAAGCTGCT
CAAGAACCAGTTAAAGGTCCTGTGTCTACTAAGCCAGGTTCTTGTCCTATTATCTTGA
TTCGTTGCGCTATGTTAAACCCACCTAACCGTTGTTTGAAGGACACTGATTGTCCAGG
TATCAAAAAGTGCTGTGAAGGTTCCTGCGGTATGGCTTGTTTCGTTCCACAAGAACAA
AAACTCATCTCAGAAGAGGATCTGTAATAGCAGCTG

Lane 1: CLD077 20h post induction
Lane 2: CLD077 3h post induction
Lane 3: CLD077 pre-induction
Lane 4: Molecular weight markers

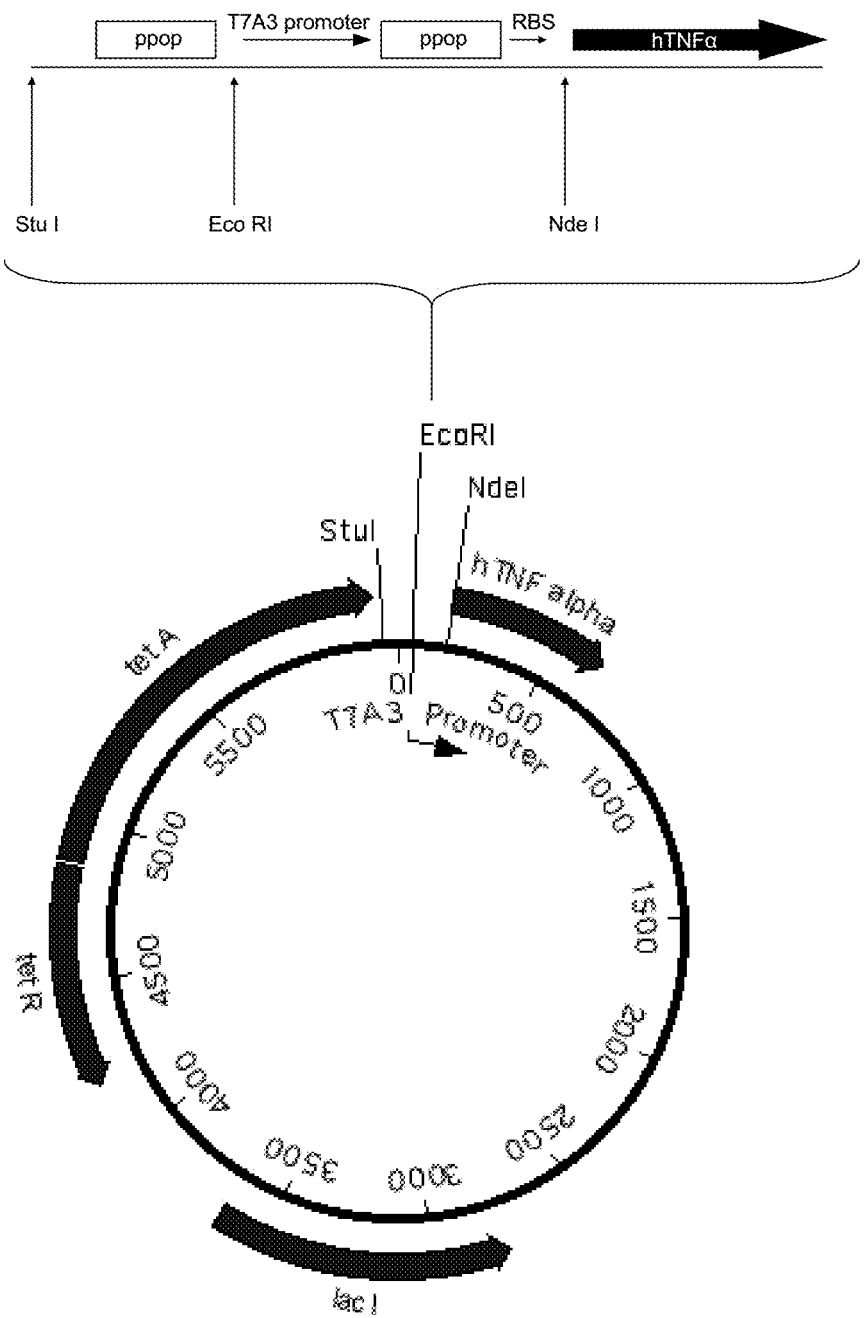
Figure 18. Plasmid map for pAVE013

SEQUENCE LISTING

```
<160> NUMBER OF SEQ ID NOS: 40

<210> SEQ ID NO 1
<211> LENGTH: 47
<212> TYPE: DNA
<213> ORGANISM: Artificial
<220> FEATURE:
<223> OTHER INFORMATION: Oligonucleotide 1 used in preparation of Linker
      12.1

<400> SEQUENCE: 1
catgtgggaa ttgtgagcgc tcacaattcc aagaacaatc ctgcacg            47

<210> SEQ ID NO 2
<211> LENGTH: 47
<212> TYPE: DNA
<213> ORGANISM: Artificial
<220> FEATURE:
<223> OTHER INFORMATION: Oligonucleotide 2.1 used in preparation of
      Linker 12.1

<400> SEQUENCE: 2
aattcgtgca ggattgttct tggaattgtg agcgctcaca attccca            47

<210> SEQ ID NO 3
<211> LENGTH: 77
<212> TYPE: DNA
<213> ORGANISM: Artificial
<220> FEATURE:
<223> OTHER INFORMATION: Oligonucleotide 3 used in cloning of T7A3
      promoter

<400> SEQUENCE: 3
aattcaaaca aaacggttga caacatgaag taaacacggt acgatgtacc ggaattgtga   60
gcgctcacaa ttcccca                                                 77

<210> SEQ ID NO 4
<211> LENGTH: 77
<212> TYPE: DNA
<213> ORGANISM: Artificial
```

-continued

<220> FEATURE:
<223> OTHER INFORMATION: Oligonucleotide 4 used in cloning of T7A3
      promoter

<400> SEQUENCE: 4 ctggtgggggg gttgtgggcg ctcgcggttc cggtgcgtcg tgccgtgttt gcttcgtgtt    60
gtcggccgtt ttgtttg                                                   77

<210> SEQ ID NO 5
<211> LENGTH: 79
<212> TYPE: DNA
<213> ORGANISM: Artificial
<220> FEATURE:
<223> OTHER INFORMATION: Oligonucleotide 11 used in preparation of
      Linker 1112

<400> SEQUENCE: 5
aattttctga aatgagctgt tgacaattaa tcatcggctc ggatactgtg tggaattgtg    60
agcggataac aattcccca                                                 79

<210> SEQ ID NO 6
<211> LENGTH: 79
<212> TYPE: DNA
<213> ORGANISM: Artificial
<220> FEATURE:
<223> OTHER INFORMATION: Oligonucleotide 12 used in preparation of
      Linker 1112

<400> SEQUENCE: 6
ctagtgggga attgttatcc gctcacaatt ccacacagta tccgagccga tgattaattg    60
tcaacagctc atttcagaa                                                 79

<210> SEQ ID NO 7
<211> LENGTH: 78
<212> TYPE: DNA
<213> ORGANISM: Artificial
<220> FEATURE:
<223> OTHER INFORMATION: Oligonucleotide 13 used in preparation of
      Linker 1314

<400> SEQUENCE: 7
aattttctga aatgagctgt tgacaattaa tcatcggctc ggatactgtg tggaattgtg    60
agcgctcaca attcccca                                                  78

<210> SEQ ID NO 8
<211> LENGTH: 78
<212> TYPE: DNA
<213> ORGANISM: Artificial
<220> FEATURE:
<223> OTHER INFORMATION: Oligonucleotide 14 used in preparation of
      Linker 1314

<400> SEQUENCE: 8
ctagtgggga attgtgagcg ctcacaattc cacacagtat ccgagccgat gattaattgt    60
caacagctca tttcagaa                                                  78

<210> SEQ ID NO 9
<211> LENGTH: 78
<212> TYPE: DNA
<213> ORGANISM: Artificial
<220> FEATURE:
<223> OTHER INFORMATION: Oligonucleotide 5 used in cloning of T7A3
      promoter

```
<400> SEQUENCE: 9
aattcgaaac aaaacggttg acaacatgaa gtaaacacgg tacgatgtac cggaattgtg    60
agcgctcaca attcccca                                                  78

<210> SEQ ID NO 10
<211> LENGTH: 78
<212> TYPE: DNA
<213> ORGANISM: Artificial
<220> FEATURE:
<223> OTHER INFORMATION: Oligonucleotide 6 used in cloning of T7A3
      Promoter

<400> SEQUENCE: 10
ctggtggggg gttgtgggcg ctcgcggttc cggtgcgtcg tgccgtgttt gcttcgtgtt    60
gtcggccgtt ttgtttcg                                                  78

<210> SEQ ID NO 11
<211> LENGTH: 77
<212> TYPE: DNA
<213> ORGANISM: Artificial
<220> FEATURE:
<223> OTHER INFORMATION: Oligonucleotide 7 used in preparation of Linker
      78

<400> SEQUENCE: 11
aattatctct ggcggtgttg acataaatac cactggcggt gatactgagc ggaattgtga    60
gcgctcacaa ttcccca                                                   77

<210> SEQ ID NO 12
<211> LENGTH: 77
<212> TYPE: DNA
<213> ORGANISM: Artificial
<220> FEATURE:
<223> OTHER INFORMATION: Oligonucleotide 8 used in preparation of Linker
      78

<400> SEQUENCE: 12
ctagtgggga attgtgagcg ctcacaattc cgctcagtat caccgccagt ggtatttatg    60
tcaacaccgc cagagat                                                   77

<210> SEQ ID NO 13
<211> LENGTH: 77
<212> TYPE: DNA
<213> ORGANISM: Artificial
<220> FEATURE:
<223> OTHER INFORMATION: Oligonucleotide 15 used in cloning of tac
      Promoter

<400> SEQUENCE: 13
aattcctgaa atgagctgtt gacaattaat catcggctcg tataatgtgt ggaattgtga    60
gcgctcacaa ttcccca                                                   77

<210> SEQ ID NO 14
<211> LENGTH: 77
<212> TYPE: DNA
<213> ORGANISM: Artificial
<220> FEATURE:
<223> OTHER INFORMATION: Oligonucleotide 16 used in cloning of tac
      Promoter
```

-continued

<400> SEQUENCE: 14
ctagtgggga attgtgagcg ctcacaattc cacacattat acgagccgat gattaattgt    60
caacagctca tttcagg                                                    77

<210> SEQ ID NO 15
<211> LENGTH: 33
<212> TYPE: DNA
<213> ORGANISM: Artificial
<220> FEATURE:
<223> OTHER INFORMATION: Oligonucleotide 19 used in preparation of EcoR
      I Linker

<400> SEQUENCE: 15
aattcaccgg tgtacagtca tgtacaaccg gtg                                  33

<210> SEQ ID NO 16
<211> LENGTH: 33
<212> TYPE: DNA
<213> ORGANISM: Artificial
<220> FEATURE:
<223> OTHER INFORMATION: Oligonucleotide 20 used in preparation of EcoR
      I Linker

<400> SEQUENCE: 16
aattcaccgg ttgtacatga ctgtacaccg gtg                                  33

<210> SEQ ID NO 17
<211> LENGTH: 1550
<212> TYPE: DNA
<213> ORGANISM: Murinae gen. sp.

<400> SEQUENCE: 17
catatgaaat acctattgcc tacggcagcc gctggattgt tattactcgc tgcccaacca      60
gcgatggccc aggtgcagct gcaggagtca ggacctggcc tggtggcgcc ctcacagagc    120
ctgtccatca catgcaccgt ctcagggttc tcattaaccg ctatggtgt aaactgggtt     180 cgccagcctc caggaaaggg tctggagtgg ctgggaatga tttggggtga tggaaacaca    240
gactataatt cagctctcaa atccagactg agcatcagca aggacaactc caagagccaa    300
gttttcttaa aaatgaacag tctgcacact gatgacacag ccaggtacta ctgtgccaga    360
gagagagatt ataggcttga ctactggggc caagggacca cggtcaccgt ctcctcagcc    420
tccaccaagg gcccatcggt cttcccctg gcaccctcct ccaagagcac ctctggggc      480 acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgactgtg ccctccagta gcttgggcac ccagacctac    660
atctgcaacg tgaatcacaa ccccagcaac accaaggtcg acaagaaagt tgagcccaaa    720
tcttcaacta agacgcacac atcaggaggt gaacagaagc tcatctcaga agaggatctg    780
aattaataag ggagcttgca tgcaaattct atttcaagga gacagtcata atgaaatacc    840
tattgcctac ggcagccgct ggattgttat tactcgctgc caaccagcg atggccgaca    900 tcgagctcac ccagtctcca gcctcccttt ctgcgtctgt gggagaaact gtcaccatca    960
catgtcgagc aagtgggaat attcacaatt atttagcatg gtatcagcag aaacagggaa   1020
aatctcctca gctcctggtc tattatacaa caaccttagc agatggtgtg ccatcaaggt   1080
tcagtggcag tggatcagga acacaatatt ctctcaagat caacagcctg caacctgaag   1140
cttttgggag ttattactgt caacattttt ggagtactcc tcggacgttc ggtggaggga   1200

```
ccaagctcga gatcaaacgg actgtggctg caccatctgt cttcatcttc ccgccatctg    1260
atgagcagtt gaaatctgga actgcctctg ttgtgtgcct gctgaataac ttctatccca    1320
gagaggccaa agtacagtgg aaggtggata acgccctcca atcgggtaac tcccaggaga    1380
gtgtcacaga gcaggacagc aaggacagca cctacagcct cagcagcacc ctgacgctga    1440
gcaaagcaga ctacgagaaa cacaaagtct acgcctgcga agtcacccat cagggcctga    1500
gttcgcccgt cacaaagagc ttcaaccgcg gagagtcata gtaaggatcc                1550
```

<210> SEQ ID NO 18
<211> LENGTH: 72
<212> TYPE: DNA
<213> ORGANISM: Artificial
<220> FEATURE:
<223> OTHER INFORMATION: Oligonucleotide 21 used in preparation of
      Linker 2122

<400> SEQUENCE: 18

```
aattcgaaac aaaacggttg acaacatgaa gtaaacacgg tacgatgtac cacatgaaac    60
gacagtgagt ca                                                         72
```

<210> SEQ ID NO 19
<211> LENGTH: 72
<212> TYPE: DNA
<213> ORGANISM: Artificial
<220> FEATURE:
<223> OTHER INFORMATION: Oligonucleotide 22 used in preparation of
      Linker 2122

<400> SEQUENCE: 19

```
ctagtgactc actgtcgttt catgtggtac ctcgtaccgt gtttacttca tgttgtcaac    60
cgttttgttt cg                                                         72
```

<210> SEQ ID NO 20
<211> LENGTH: 79
<212> TYPE: DNA
<213> ORGANISM: Artificial
<220> FEATURE:
<223> OTHER INFORMATION: Oligonucleotide 23 used in preparation of
      Linker 2324

<400> SEQUENCE: 20

```
aattcgaaac aaaacggttg acaacatgaa gtaaacacgg tacgatgtac cggaattgtg    60
agcggataac aattcccca                                                  79
```

<210> SEQ ID NO 21
<211> LENGTH: 79
<212> TYPE: DNA
<213> ORGANISM: Artificial
<220> FEATURE:
<223> OTHER INFORMATION: Oligonucleotide 24 used in preparation of
      Linker 2324

<400> SEQUENCE: 21

```
ctagtgggga attgttatcc gctcacaatt ccggtacatc gtaccgtgtt tacttcatgt    60
tgtcaaccgt tttgtttcg                                                  79
```

<210> SEQ ID NO 22
<211> LENGTH: 1592
<212> TYPE: DNA
<213> ORGANISM: Artificial
<220> FEATURE:
<223> OTHER INFORMATION: Sequence encoding bispecific single chain
      tetravalent diabody produced in Example 15

<400> SEQUENCE: 22

```
catatgaaaa agacagctat cgcgattgca gtggcactgg ctggtttcgc taccgtagct      60
caagcccagg tgcagctgca ggagtcagga cctggcctgg tggcgccctc acagagcctg     120
tccatcacat gcaccgtctc agggttctca ttaaccggct atggtgtaaa ctgggttcgc     180
cagcctccag gaaagggtct ggagtggctg ggaatgattt ggggtgatgg aaacacagac     240
tataattcag ctctcaaatc cagactgagc atcagcaagg acaactccaa gagccaagtt     300
ttcttaaaaa tgaacagtct gcacactgat gacacagcca ggtactactg tgccagagag     360
agagattata ggcttgacta ctggggccaa gggaccacgg tcaccgtctc ctcagcctcc     420
accaagggcc catcgagcgc caaaaccacc ccggacatcg agctctccca gtctccagca     480
atcctgtctg catctccagg ggagaaggtc acaatgactt gcagggccag ctcaagtgta     540
acttacattc actggtacca gcagaagcca ggatcctccc ccaaatcctg gatttatgcc     600
acatccaacc tggcttctgg agtccctgct cgcttcagtg gcagtgggtc tgggacctct     660
tactctctca caatcagcag agtggaggct gaagatgctg ccacttatta ctgccaacat     720
tggagtagta aaccaccgac gttcggtgga ggcaccaagc tcgagatcaa acggactgtg     780
cgcgccgatg ccgccccgac cgtgcaggtg cagctgcagg aatctggtgg tggcttagtt     840
caacctggtg gttccctgag actctcctgt gcaacttctg ggttcacctt cactgattac     900
tacatgaact gggtccgcca gcctccagga aaggcacttg agtggttggg ttttattgga     960
aacaaagcta atggttacac aacagagtac agtgcatctg tgaagggtcg gttcaccatc    1020
tccagagata atcccaaag catcctctat cttcaaatga cacccctgag agctgaggac    1080
agtgccactt attactgtac aagagatagg gggctacggt tctactttga ctactgggc    1140
caaggcacca cggtcaccgt ctcctcagcc tccaccaagg gcccatcgag cgccaaaacc    1200
accccggaca tcgagctcac ccagtctcca gcctcccttt ctgcgtctgt gggagaaact    1260
gtcaccatca catgtcgagc aagtgggaat attcacaatt atttagcatg gtatcagcag    1320
aaacagggaa aatctcctca gctcctggtc tattatacaa caaccttagc agatggtgtg    1380
ccatcaaggt tcagtggcag tggatcagga acacaatatt ctctcaagat caacagcctg    1440
caacctgaag cttttgggag ttattactgt caacatttt ggagtactcc tcggacgttc    1500
ggtggaggga ccaagctcga gatcaaacgg actgtgggat ccgaacaaaa gctgatctca    1560
gaagaagacc taaactcatg ataagcggcc gc                                   1592
```

<210> SEQ ID NO 23
<211> LENGTH: 1237
<212> TYPE: DNA
<213> ORGANISM: Artificial
<220> FEATURE:
<223> OTHER INFORMATION: Sequence encoding GST fusion protein produced
      in Example 16

<400> SEQUENCE: 23

```
catatgtccc ctatactagg ttattggaaa attaagggcc ttgtgcaacc cactcgactt      60
cttttggaat atcttgaaga aaatatgaa gagcatttgt atgagcgcga tgaaggtgat     120
aaatggcgaa acaaaaagtt tgaattgggt ttggagtttc ccaatcttcc ttattatatt     180
gatggtgatg ttaaattaac acagtctatg gccatcatac gttatatagc tgacaagcac     240
```

```
aacatgttgg gtggttgtcc aaaagagcgt gcagagattt caatgcttga aggagcggtt      300
ttggatatta gatacggtgt ttcgagaatt gcatatagta aagactttga aactctcaaa      360
gttgattttc ttagcaagct acctgaaatg ctgaaaatgt tcgaagatcg tttatgtcat      420
aaaacatatt taaatggtga tcatgtaacc catcctgact tcatgttgta tgacgctctt      480
gatgttgttt tatacatgga cccaatgtgc ctggatgcgt tcccaaaatt agtttgtttt      540
aaaaaacgta ttgaagctat cccacaaatt gataagtact tgaaatccag caagtatata      600
gcatggcctt tgcagggctg gcaagccacg tttggtggtg gcgaccatcc tccaaaatcg      660
gatctggttc cgcgtggatc cggaccaaac acagaatttg cactatccct gttaaggaaa      720
aacataatga ctataacaac ctcaaaggga gagttcacag ggttaggcat acatgatcgt      780
gtctgtgtga tacccacaca cgcacagcct ggtgatgatg tactagtgaa tggtcagaaa      840
attagagtta aggataagta caaattagta gatccagaga acattaatct agagcttaca      900
gtgttgactt tagatagaaa tgaaaaattc agagatatca ggggatttat atcagaagat      960
ctagaaggtg tggatgccac tttggtagta cattcaaata actttaccaa cactatctta     1020
gaagttggcc ctgtaacaat ggcaggactt attaatttga gtagcacccc cactaacaga     1080
atgattcgtt atgattatgc aacaaaaact gggcagtgtg gaggtgtgct gtgtgctact     1140
ggtaagatct ttggtattca tgttggcggt aatggaagac aaggattttc agctcaactt     1200
aaaaaacaat attttgtaga gaaacaataa gaattcc                             1237

<210> SEQ ID NO 24
<211> LENGTH: 513
<212> TYPE: DNA
<213> ORGANISM: Homo sapiens

<400> SEQUENCE: 24
catatgatgt gtgatctgcc gcaaactcat agcctgggta gccgtcgcac cctgatgctg       60
ctggcccaaa tgcgccgtat ctccctgttc tcctgtctga agaccgcca tgactttggc      120 ttcccgcagg aagagttcgg taaccagttc caaaaggcag aaactatccc ggtactgcac      180
gaaatgattc aacagatttt taacctgttc agcactaaag actcctctgc tgcatgggac      240
gaaactctcc tggacaaaat tctacaccga actgtaccag caactgaacga cctggaagcc      300 tgcgtcatcc agggtgttgg cgtaaccgaa actccgctga tgaaagaaga ctccatcctg      360
gctgttcgca atacttcca gcgtatcacc ctgtacctga agagaagaa atacagcccg        420 tgcgcttggg aagttgtacg cgctgaaatc atgcgttcct tcagcctgtc cactaacctg      480
caagaatctc tgcgtagcaa agaataactc gag                                  513

<210> SEQ ID NO 25
<211> LENGTH: 517
<212> TYPE: DNA
<213> ORGANISM: Homo sapiens

<400> SEQUENCE: 25
catatggctc cgccacgtct gatttgtgac tctcgcgttc tggagcgtta cctgctggag       60
gccaaggaag ccgaaaacat cacgaccggt tgtgcggaac attgctctct gaatgagaac      120
atcactgttc cggatacgaa ggttaacttc tacgcttgga acgtatggaa agtaggccag      180
caggcagtag aagtgtggca gggtctggcg ctgctgtccg aagcggttct gcgtggccag      240
gcgctgctga tcaactccag ccagccgtgg gagccgctgc agctgcacgt agataaagcg      300
gttagcggtc tgcgttccct gactaccctg ctgcgcgcgc tgggtgcgca aaaagaagct     360
```

```
atctccccgc agatgcggc atctgcagcc ccgctgcgta ccatcactgc agatactttc    420
cgcaagctgt tcgtgttta ttccaacttc ctgcgtggta aactgaagct gtacaccggt    480
gaagcgtgcc gtaccggcga tcgttaataa actcgag                            517
```

```
<210> SEQ ID NO 26
<211> LENGTH: 713
<212> TYPE: DNA
<213> ORGANISM: Pseudomonas putida

<400> SEQUENCE: 26
catatgaagg aaataaccaa tgaaaaacat ccaaggtatc gttttcgatt tgtatggcac     60
gctctacgac gtgcattccg tggtgcaagc ctgtgaagag gtctatccgg gccaaggcga    120
cgctatttct cgcctctggc ggcaaaagca attggaatac acctggctca ggagcctcat    180
gggccgttac gtgaactttg agaaagcaac agaggatgcc ttgcgcttta cctgcacgca    240
tctgggcttg tcgctcgatg atgaaaccca ccagcgcctc agtgatgctt atttgcacct    300
caccccttat gccgatacag ctgacgccgt tcgccgtttg aaagctgcgg gcctaccgct    360
aggcatcatt tcaaatggtt ctcattgctc gatcgagcaa gtcgtgacta actctgaaat    420
gaattgggcg ttcgatcagc tgatcagcgt cgaggatgtg caagtgttca acctgatag    480 tcgcgtctat agccttgccg agaagcgcat gggttttcca aaggaaaaca tcctcttcgt    540
ttcgtcaaac gcgtgggatg cgagtgcagc cagtaacttt ggtttcccgg tttgctggat    600
caatcggcag aacggcgcgt tgatgagct ggatgcaaag ccgacacacg tcgtgcgtaa    660
tctcgccgaa atgtcgaact ggctggttaa ttcgctcgat taatgaagga tcc          713
```

```
<210> SEQ ID NO 27
<211> LENGTH: 26
<212> TYPE: DNA
<213> ORGANISM: Artificial
<220> FEATURE:
<223> OTHER INFORMATION: F37A Primer used in Example 17

<400> SEQUENCE: 27
agatctacgc ttatgggtgc ctttcc                                         26
```

```
<210> SEQ ID NO 28
<211> LENGTH: 26
<212> TYPE: DNA
<213> ORGANISM: Artificial
<220> FEATURE:
<223> OTHER INFORMATION: B29a Primer used in Example 17

<400> SEQUENCE: 28
agatctaata cgcaaaccgc ctctcc                                         26
```

```
<210> SEQ ID NO 29
<211> LENGTH: 69
<212> TYPE: DNA
<213> ORGANISM: Artificial
<220> FEATURE:
<223> OTHER INFORMATION: Oligonucleotide GalB1 used in preparation of
      GalB Linker

<400> SEQUENCE: 29
aattcatacc ataagcctaa ttctacgaat tatcagagtt ctggttaccg gtgtaagcgc     60
ttacactgt                                                            69
```

```
<210> SEQ ID NO 30
<211> LENGTH: 69
<212> TYPE: DNA
<213> ORGANISM: Artificial
<220> FEATURE:
<223> OTHER INFORMATION: Oligonucleotide GalB2 used in preparation of
      GalB Linker

<400> SEQUENCE: 30
ctagacagtg taagcgctta caccggtaac cagaactctg ataattcgta gaattaggct    60
tatggtatg                                                           69

<210> SEQ ID NO 31
<211> LENGTH: 68
<212> TYPE: DNA
<213> ORGANISM: Artificial
<220> FEATURE:
<223> OTHER INFORMATION: Oligonucleotide GalA1 used in preparation of
      GalA Linker

<400> SEQUENCE: 31
caattgtgta agcgcttaca caactttatt ccatgtcaca cttttcgcat ctttgttatg    60
ctatggtg                                                            68

<210> SEQ ID NO 32
<211> LENGTH: 72
<212> TYPE: DNA
<213> ORGANISM: Artificial
<220> FEATURE:
<223> OTHER INFORMATION: Oligonucleotide GalA2 used in preparation of
      GalA Linker

<400> SEQUENCE: 32
aattcaccat cgcataacaa ggatgcgaaa agtgtgacat ggaataaagt tgtgtaagcg    60
cttacacaat tg                                                       72

<210> SEQ ID NO 33
<211> LENGTH: 438
<212> TYPE: DNA
<213> ORGANISM: Artificial
<220> FEATURE:
<223> OTHER INFORMATION: Sequence encoding hCMV Promoter and Lac
      Operators used in Example 21

<400> SEQUENCE: 33
catatgccaa gtccgccccc tattgacgtc aatgacggta aatggcccgc ctggcattat    60
gcccagtaca tgaccttacg ggactttcct acttggcagt acatctacgt attagtcatc   120
gctattatac catggtgatg cggttttggc agtacaccaa tgggcgtgga tagcggtttg   180
actcacgggg atttccaagt ctccacccca ttgacgtcaa tgggagtttg ttttggcacc   240
aaaatcaacg ggactttcca aaatgtcgta ataaccccgc cccgttgacg caaatgggga   300
attgtgagcg ctcacaattc ctctatataa gcagagctcg tttagtgaac cgtcagatca   360
ctagatgcgt acagtccgat gacttgcatg gaattgtgag cgctcacaat tccaagcttt   420
attgcggtat aggctagc                                                 438

<210> SEQ ID NO 34
<211> LENGTH: 813
<212> TYPE: DNA
<213> ORGANISM: Artificial
<220> FEATURE:
<223> OTHER INFORMATION: Sequence encoding IgG Fc protein used in
      Example 21
```

<400> SEQUENCE: 34

```
atggagacag acacactcct gctatgggta ctgctgctct gggttccagg ttccactggt    60
gacgcggccc agccggccag gcgcgcgcgc cgtacgtaca agcttggatc cgcagagccc   120
aaatcttgtg acaaaactca cacatgccca ccgtgcccag cacctgaact cctgggggga   180
ccgtcagtct tcctcttccc cccaaaaccc aaggacaccc tcatgatctc ccggacccct   240
gaggtcacat gcgtggtggt ggacgtgagc cacgaagacc ctgaggtcaa gttcaactgg   300
tacgtggacg gcgtggaggt gcataatgcc aagacaaagc cgcgggagga gcagtacaac   360
agcacgtacc gtgtggtcag cgtcctcacc gtcctgcacc aggactggct gaatggcaag   420
gagtacaagt gcaaggtctc caacaaagcc ctcccagccc catcgagaaa accatctcc   480
aaagccaaag gcagccccg agaaccacag gtgtacaccc tgcccccatc ccgggatgag   540
ctgaccaaga accaggtcag cctgacctgc ctggtcaaag gcttctatcc cagcgacatc   600
gccgtggagt gggagagcaa tgggcagccg gagaacaact acaagaccac gcctcccgtg   660
ctggactccg acggctcctt cttcctctac agcaagctca ccgtggacaa gagcaggtgg   720
cagcagggga acgtcttctc atgctccgtg atgcatgagg ctctgcacaa ccactacacg   780
cagaagagcc tctccctgtc tccgggtaaa tga                                813
```

<210> SEQ ID NO 35
<211> LENGTH: 1104
<212> TYPE: DNA
<213> ORGANISM: Artificial
<220> FEATURE:
<223> OTHER INFORMATION: Clone Sequence 1 used in Example 20

<400> SEQUENCE: 35

```
ctcgaggcat gtgctctgta tgtatataaa actcttgttt tcttcttttc tctaaatatt    60
ctttccttat acattaggac ctttgcagca taaattacta tacttctata gacacgcaaa   120
cacaaataca cacactaaat ggcggagctg aattacattc ccaaccgcgt ggcacaacaa   180
ctggcgggca aacagtcgtt gctgattggc gttgccacct ccagtctggc cctgcacgcg   240
ccgtcgcaaa ttgtcgcggc gattaaatct cgcgccgatc aactgggtgc cagcgtggtg   300
gtgtcgatgg tagaacgaag cggcgtcgaa gcctgtaaag cggcggtgca caatcttctc   360
gcgcaacgcg tcagtgggct gatcattaac tatccgctgg atgaccagga tgccattgct   420
gtggaagctg cctgcactaa tgttccggcg ttatttcttg atgtctctga ccagacaccc   480
atcaacagta ttattttctc ccatgaagac ggtacgcgac tgggcgtgga gcatctggtc   540
gcattgggtc accagcaaat cgcgctgtta gcgggcccat taagttctgt ctcggcgcgt   600
ctgcgtctgg ctggctggca taaatatctc actcgcaatc aaattcagcc gatagcggaa   660
cgggaaggcg actggagtgc catgtccggt tttcaacaaa ccatgcaaat gctgaatgag   720
ggcatcgttc ccactgcgat gctggttgcc aacgatcaga tggcgctggg cgcaatgcgc   780
gccattaccg agtccgggct gcgcgttggt gcggatatct cggtagtggg atacgacgat   840
accgaagaca gctcatgtta tcccgccg ttaaccacca tcaaacagga ttttcgcctg   900
ctggggcaaa ccagcgtgga ccgcttgctg caactctctc agggccaggc ggtgaagggc   960
aatcagcttt tgcccgtctc actggtgaaa agaaaaacca ccctggcgcc caatacgcaa  1020
accgcctctc cccgcgcgtt ggccgattca ttaatgcagc tcgcacgaca ggtttcccga  1080
ctggaaagcg ggcagtgact cgag                                         1104
```

```
<210> SEQ ID NO 36
<211> LENGTH: 1026
<212> TYPE: DNA
<213> ORGANISM: Artificial
<220> FEATURE:
<223> OTHER INFORMATION: Clone sequence 2 used in Example 20

<400> SEQUENCE: 36
ggatcctagg caataattat gagataaatg gtgcagcact attaagtagt gtggatttca      60
ataatttccg aattaggaat aaatgcgcta aatagacatc ccgttctctt tggtaatctg     120
cataattctg atgcaatatc caacaactat ttgtgcaatt atttaacaaa atccaattaa     180
ctttcctaat tagtccttca atagaacatc tgtattcctt ttttttatga acaccttcct     240
aattaggcca tcaacgacag taaattttgc cgaatttaat agcttctact gaaaaacagt     300
ggaccatgtg aaaagatgca tctcatttat caaaacacata atattcaagt gagccttact     360
tcaattgtat tgaagtgcaa gaaaaccaaa agcaacaac aggttttgga taagtacata      420
tataagggaa ttgtgagcgc tcacaattcc tgttactgtt cttacgattc atttacgatt     480
caagaatagt tcaaacaaga agattacaaa ctatcaatgg aattgtgagc gctcacaatt     540
ccaagaatga gatttccttc aattttact gctgttttat tcgcagcatc ctccgcatta      600
gctgctccag tcaacactac aacagaagat gaaacggcac aaattccggc tgaagctgtc     660
atcggttact cagatttaga aggggatttc gatgttgctg ttttgccatt ttccaacagc     720
acaaataacg ggttattgtt tataaatact actattgcca gcattgctgc taaagaagaa     780
ggggtatctc tcgagaaaag agaggctgaa gctgctcaag aaccagttaa aggtcctgtg     840
tctactaagc caggttcttg tcctattatc ttgattcgtt gcgctatgtt aaacccacct     900
aaccgttgtt tgaaggacac tgattgtcca ggtatcaaaa agtgctgtga aggttcctgc     960
ggtatggctt gtttcgttcc acaagaacaa aaactcatct cagaagagga tctgtaatag    1020
cagctg                                                              1026

<210> SEQ ID NO 37
<211> LENGTH: 78
<212> TYPE: DNA
<213> ORGANISM: Artificial
<220> FEATURE:
<223> OTHER INFORMATION: Oligonucleotide 17 used in cloning of tac
      Promoter

<400> SEQUENCE: 37
aattttctga aatgagctgt tgacaattaa tcatcggctc gtataatgtg tggaattgtg      60
agcgctcaca attcccca                                                   78

<210> SEQ ID NO 38
<211> LENGTH: 78
<212> TYPE: DNA
<213> ORGANISM: Artificial
<220> FEATURE:
<223> OTHER INFORMATION: Oligonucleotide 18 used in cloning of tac
      Promoter

<400> SEQUENCE: 38
ctagtgggga attgtgagcg ctcacaattc cacacattat acgagccgat gattaattgt      60
caacagctca tttcagaa                                                   78
```

```
<210> SEQ ID NO 39
<211> LENGTH: 78
<212> TYPE: DNA
<213> ORGANISM: Artificial
<220> FEATURE:
<223> OTHER INFORMATION: Oligonucleotide 9 used in cloning of lambda pL
      Promoter

<400> SEQUENCE: 39
aattcatctc tggcggtgtt gacataaata ccactggcgg tgatactgag cggaattgtg      60
agcgctcaca attcccca                                                    78

<210> SEQ ID NO 40
<211> LENGTH: 78
<212> TYPE: DNA
<213> ORGANISM: Artificial
<220> FEATURE:
<223> OTHER INFORMATION: Oligonucleotide 10 used in cloning of lambda pL
      Promoter

<400> SEQUENCE: 40
ctagtgggga attgtgagcg ctcacaattc cgctcagtat caccgccagt ggtatttatg      60 tcaaccgc cagagatg                                                      78
```

EXPRESSION SYSTEM

SEQUENCE LISTING SUBMISSION VIA EFS-WEB

A computer readable text file, entitled "SequenceListing.txt," created on or about Aug. 1, 2008 with a file size of about 22 kb contains the sequence listing for this application and is hereby incorporated by reference in its entirety.

The present invention concerns an expression system suitable for the microbial expression of recombinant polypeptides.

T7-based perfect palindrome operator sequence-based protein expression systems are known from U.S. Pat. No. 6,537,779. T7 based systems suffer from drawbacks in that operation of the T7 system requires phage polymerase which is commonly provided by inserting a λDE3 prophage expressing the required phage polymerase into the *Escherichia coli* host strain to create lysogenic host strains. The phage polymerase can also be delivered to the cell by infection with a specialised λ transducing phage that carries the gene for the phage polymerase (e.g. T7 RNA polymerase). The λDE3 prophage lacks the genetic elements required for the excision of the prophage to form lytic phage particles. However, λDE3 lysogenic host strains have been shown to release phage particles and thus cause undesirable infections in fermentation plants. Indeed, the use of λDE3 strains is not permitted by certain fermentation plant operators.

Expression of the heterologous protein prior to induction is not desirable because some heterologous proteins have deleterious effects on the host cell growth and plasmid stability which reduce overall productivity. To avoid this, T7-based expression systems generally control expression of heterologous proteins at two levels. First, induction of expression of the T7 RNA polymerase gene to produce T7 RNA polymerase is required to drive expression from the T7 promoter. Secondly, the T7 promoter itself also needs to be induced. This increases the complexity of operating T7-based expression systems.

There are a large number of heterologous protein expression systems with different modes of control and induction, making selection and optimisation of the expression system/fermentation process for proteins of interest a largely empirical process. This is time consuming and undesirable. Thus, there is a need for systems which can provide improved control of expression and improved levels of protein expression without the use of phage polymerase and lysogenic host strains. There is also a need for systems which can provide inducible heterologous expression in prokaryotic cells, as well as eukaryotic cells such as mammalian and yeast cells.

According to the present invention, there is provided a perfect palindrome operator sequence-based protein expression system comprising:
  a) a promoter; and
  b) a perfect palindrome operator sequence;
  characterised in that the promoter is not T7.

Promoters which can be employed in the expression system of the present invention are commonly host RNA polymerase-based promoter systems, and preferably *E. coli* RNA polymerase-based promoter systems. Examples of promoters which can be employed include T7A1, T7A2, T7A3, λpL, λpR, lac, lacUV5, trp, tac, trc, phoA and rrnB.

Operator sequences which may be employed in the expression system according to the present invention include lac, gal, deo and gln. One or more perfect palindrome operator sequences may be employed. In many preferred embodiments, two perfect palindrome operator sequences are employed, most advantageously one operator sequence being located downstream of the promoter, and one operator sequence being located upstream of the promoter. When two operator systems are employed, the operator sequences are preferably spaced to maximise control of the promoter. In many embodiments, the spacing is from 85 to 150 base pairs apart, preferably from 90 to 126 base pairs apart, and most preferably 91 or 92 base pairs apart. In certain embodiments, an operator sequence overlaps with the transcriptional start point It will be recognised that the operator system is commonly employed with an appropriate repressor sequence. Repressor sequences produce repressor protein, for example lad gene sequence when using the lac operators. Other lac repressor sequences may also be used, for example the lacI$^Q$ sequence can be used to increase the level of lac repressor protein. The repressor sequence may also be provided by the host cell genome or by using an additional compatible plasmid.

The expression system may be integrated into the host cell genome, but is preferably comprised within an extrachromosomal element such as a plasmid. Alternatively, the expression system may be incorporated into phage or viral vectors and these used to deliver the expression system into the host cell system. Plasmids or expression vectors can be assembled by methods known in the art. The plasmid typically also comprises one or more of the following: a selectable marker, for example a sequence conferring antibiotic resistance, a cer stability sequence and an expression cassette. The expression system may also incorporate a signal sequence if secretion of the desired protein is required.

Expression may be induced by the addition of an inducer such as isopropyl-β-D-1-thiogalactopyranoside (IPTG), analogues of IPTG such as isobutyl-C-galactoside (IBCG), lactose or melibiose. Other inducers may be used and are described more fully elsewhere (e.g. see The Operon, eds Miller and Renznikoff (1978)). Inducers may be used individually or in combination. The construction of appropriate plasmids or expression vectors will be apparent to the scientist of ordinary skill.

The expression system of the present invention can be employed to express proteins in host cells, and especially in microorganisms. As used herein, "proteins" refers generally to peptides and proteins having more than about 10 amino acids. The host cell may be prokaryotic or eukaryotic. Examples of prokaryotic cells include bacterial cells, for example gram-negative bacterial cells, including *E. coli, Salmonella typhimurium, Serratia marsescens* and *Pseudomonas aeruginosa*, and gram-positive bacterial cells including *Bacillus subtilis*. Examples of eukaryotic cells include yeasts, such as *Pichia pastoris, Saccharomyces cerevisiae, Hansenula polymorpha, Kluyveromyces lactis, Schizosaccharomyces pombe*. Mammalian host cells which can be employed include human cell lines, such as human embryonic kidney and PERC.6 cells; murine cell lines, such as NS0 cells; and particularly hamster cell lines such as baby hamster kidney cells and especially Chinese hamster ovary cells. Other eukaryotic host cells such as those of filamentous fungi, plant, insect, amphibian cells or ovarian species may also be employed. Preferred host cells are bacteria, particularly enterobacteriacae, preferably *E coli*, and especially B or K12 strains thereof.

The expression system of the present invention is commonly employed in the form of a plasmid, and plasmids comprising a promoter and a perfect palindrome operator sequence, wherein the promoter is not T7, form another aspect of the present invention. The plasmids may be autonomously replicating plasmids or integrative plasmids.

The expression system of the present invention is advantageously employed for the manufacture of proteins, especially recombinant proteins, by culturing recombinant cells. For the expression of proteins, it will be recognised that the promoter and operator sequence are operably linked to DNA encoding a protein to be expressed.

Accordingly, the present invention also provides a method for the production of a protein which comprises expressing an expression system comprising
a) a promoter;
b) a perfect palindrome operator sequence; and
c) an expression cassette for a protein;
characterised in that the promoter is not T7.

One or more promoters, operator sequences and expression cassettes, which may be the same or different, may be present if desired.

The expression system is expressed by methods well known in the art for the cells employed. Preferred expression methods include culturing the recombinant cells in growth medium, especially by fermentation, and then recovering the expressed protein. The term "growth medium" refers to a nutrient medium used for growing the recombinant cells. In many embodiments, a nutrient solution is employed. Suitable growth media for given recombinant cells are well known in the art.

The present invention is illustrated without limitation by the following examples.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings:

FIG. 1 is a D1.3 Fab expression cassette according to an embodiment of the present invention;

FIG. 5 shows the DNA sequence for a synthetic bispecific single chain tetravalent diabody (bsctDb) that was designed according to Example 15;

FIG. 6 shows SEQ ID NO: 23 according to Example 16;
FIG. 7 shows SEQ ID NO: 24 according to Example 16;
FIG. 8 shows SEQ ID NO: 25 according to Example 16;
FIG. 9 shows SEQ ID NO: 26 according to Example 17;
FIG. 11 shows the growth of CLD075 and expression/accumulation of HadL protein following induction according to Example 18;
FIG. 12 shows SEQ ID NO: 33 according to Example 21;
FIG. 13 shows SEQ ID NO: 34 according to Example 21;
FIG. 15 shows SEQ ID NO: 35 according to Example 20;
FIG. 16 shows SEQ ID NO: 36 according to Example 20;

FIG. 18 shows a plasmid map for pAVE013 according to an embodiment of the present invention.

1. GENERATION OF DAVE SERIES OF VECTORS

Vectors pAVE011, pAVE012 and pAVE013

Figure 2:
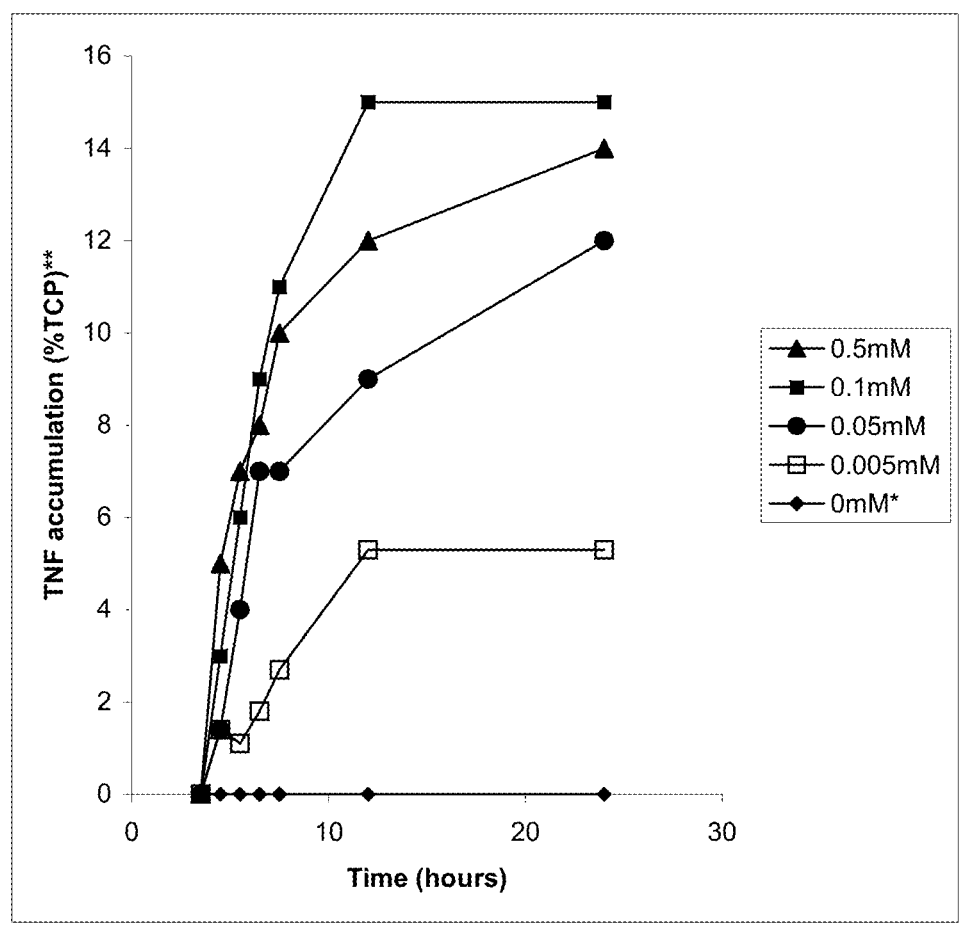
FIG. 2 shows the result of the accumulation level of hTNFα according to Example 7.

The starting vector for the generation of pAVE011 was pZT7#2.0, prepared as described in U.S. Pat. No. 6,537,779. pZT7#2.0 has a pAT153 vector backbone, cer stability sequence, tet A/R, a single native lac operator sequence upstream of the gene of interest and an upstream T4 transcription terminator. A T7A3 promoter and dual perfect palindrome lac operators were cloned into this plasmid using synthetic oligonucleotide linkers by means of the Nco 1, EcoR I and Xba 1 restriction enzyme sites.

Linker 12.1 was prepared by annealing the oligonucleotides 1 and 2.1:

```
Oligonucleotide 1
                                        (SEQ ID NO 1)
5'CATGTGGGAATTGTGAGCGCTCACAATTCCAAGAACAATCCTGCACG Oligonucleotide 2.1
                                        (SEQ ID NO 2)
5'AATTCGTGCAGGATTGTTCTTGGAATTGTGAGCGCTCACAATTCCCA
```

The linker was then ligated to plasmid pZT7#2.0 and transformed into cloning host strain XL-1 Blue MR (Stratagene) as an Nco 1/EcoR I fragment. Initial screening of transformants was by restriction digestion using Nco 1. The sequence was confirmed by sequencing. The resultant plasmid was named pAVE012.

The T7A3 promoter cassette was then cloned into pAVE012 by annealing oligonucleotides 3 and 4:

```
Oligonucleotide 3
                                        (SEQ ID NO 3)
5'AATTCAAACAAAACGGTTGACAACATGAAGTAAACACGGTACGATGTA
CCGGAATTGTGAGCGCTCACAATTCCCCA Oligonucleotide 4
                                        (SEQ ID NO 4)
5'CTGGTGGGGGTTGTGGGCGCTCGCGGTTCCGGTGCGTCGTGCCGT
GTTTGCTTCGTGTTGTCGGCCGTTTTGTTTG
``` the annealed oligonucleotides being ligated to plasmid pAVE012 and transformed into cloning host strain XL-1 Blue MR (Stratagene) as an Xba 1/EcoR I fragment. Initial screening was by restriction digest of plasmid DNA. The sequence was then confirmed by sequencing. The resultant plasmid was named pAVE011.

Human TNFα gene was cloned into this plasmid as an Nde I/Xho I fragment to generate pAVE013. A plasmid map for pAVE013 is presented in FIG. 18. This shows the arrangement of operators and promoter, and the restriction enzyme sites used in the construction. The operators are both perfect palindrome lac operators. RBS is the ribosomal binding site. The vector includes a pAT153 vector backbone, a cer stability sequence, an inducible tetracycline resistance gene (tet A/R), and an upstream T4 transcription terminator.

Vectors pAVE038 and pAVE041

The starting vector for the generation of pAVE038 was pZT7#2.0, prepared as described in U.S. Pat. No. 6,537,779. A tac promoter and single native lac operator were cloned into this plasmid using a synthetic oligonucleotide linker by means of the EcoR I and Xba I restriction enzyme sites.

Linker 1112 was made by annealing the oligonucleotides 11 and 12

Oligonucleotide 11
(SEQ ID NO 5)
5'AATTTTCTGAAATGAGCTGTTGACAATTAATCATCGGCTCGGATACTG
TGTGGAATTGTGAGCGGATAACAATTCCCCA Oligonucleotide 12
(SEQ ID NO 6)
5'CTAGTGGGGAATTGTTATCCGCTCACAATTCCACACAGTATCCGAGCC
GATGATTAATTGTCAACAGCTCATTTCAGAA The linker was then ligated to plasmid pZT7#2.0 and transformed into cloning host strain XL-1 Blue MR (Stratagene) as an Xba 1/EcoR I fragment. Initial screening of transformants was by restriction digestion using Nco 1. The sequence was confirmed by sequencing. The resultant plasmid was named pAVE038.

A human TNFα gene was cloned into this plasmid as an Nde I/Xho I fragment to generate plasmid pAVE041.

Vector pAVE037 and pAVE040

The starting vector for the generation of pAVE037 was pZT7#2.0 prepared as described in U.S. Pat. No. 6,537,779. A tac promoter and single perfect palindrome lac operator were cloned into this plasmid using a synthetic oligonucleotide linker by means of the EcoR I and Xba 1 restriction enzyme sites.

Linker 1314 was made by annealing the oligonucleotides 13 and 14

Oligonucleotide 13
(SEQ ID NO 7)
5'AATTTTCTGAAATGAGCTGTTGACAATTAATCATCGGCTCGGATACT
GTGTGGAATTGTGAGCGCTCACAATTCCCCA Oligonucleotide 14
(SEQ ID NO 8)
5'CTAGTGGGGAATTGTGAGCGCTCACAATTCCACACAGTATCCGAGCC
GATGATTAATTGTCAACAGCTCATTTCAGAA The linker was then ligated to plasmid pZT7#2.0 and transformed into cloning host strain XL-1 Blue MR (Stratagene) as an Xba 1/EcoR I fragment. Initial screening of transformants was by restriction digestion using Nco 1. The sequence was confirmed by sequencing. The resultant plasmid was named pAVE037.

A human TNFα gene was cloned into this plasmid as an Nde I/Xho I fragment to generate pAVE040.

Vector pAVE028 and pAVE030

The starting vector for the generation of pAVE028 was pAVE012. A T7A3 promoter cassette was cloned into pAVE012 by annealing oligonucleotides 5 and 6.

Oligonucleotide 5
(SEQ ID NO 9)
5'AATTCGAAACAAAACGGTTGACAACATGAAGTAAACACGGTACGATG
TACCGGAATTGTGAGCGCTCACAATTCCCCA Oligonucleotide 6
(SEQ ID NO 10)
5'CTGGTGGGGGGTTGTGGGCGCTCGCGGTTCCGGTGCGTCGTGCCGT
GTTTGCTTCGTGTTGTCGGCCGTTTTGTTTCG the annealed oligonucleotides being ligated to plasmid pAVE012 and transformed into cloning host strain XL-1 Blue MR (Stratagene) as an Xba 1/EcoR I fragment. Initial screening was by restriction digest of plasmid DNA. The sequence was then confirmed by sequencing. The resultant plasmid was named pAVE028.

A human TNFα gene was cloned into this plasmid as an Nde I/Xho I fragment to generate pAVE030.

Vector pAVE007 and pAVE031

The starting vector for the generation of pAVE007 was pZT7#2.0 prepared as described in U.S. Pat. No. 6,537,779. A T7A3 promoter and single perfect palindrome lac operator was cloned into this plasmid using a synthetic oligonucleotide linker by means of the EcoR I and Xba 1 restriction enzyme sites.

The linker containing the T7A3 promoter was made up of oligonucleotides 3 and 4.

Oligonucleotide 3
(SEQ ID NO 3)
5'AATTCAAACAAAACGGTTGACAACATGAAGTAAACACGGTACGATGT
ACCGGAATTGTGAGCGCTCACAATTCCCCA Oligonucleotide 4
(SEQ ID NO 4)
5'CTGGTGGGGGGTTGTGGGCGCTCGCGGTTCCGGTGCGTCGTGCCGT
GTTTGCTTCGTGTTGTCGGCCGTTTTGTTTG Oligonucleotides 3 and 4 were annealed, the linker formed was then ligated to plasmid pZT7#2.0 and transformed into cloning host strain XL-1 Blue MR (Stratagene) as an Xba 1/EcoR I fragment. Initial screening was by restriction digest of plasmid DNA. The sequence was then confirmed by sequencing. The resultant plasmid was named pAVE007.

A human TNFα gene was cloned into this plasmid as an Nde I/Xho I fragment to generate pAVE031.

Vectors pAVE029 and pAVE027

The starting vector for the generation of pAVE029 was pZT7#2.0 prepared as described fully in U.S. Pat. No. 6,537,779. A λpL promoter and single perfect palindrome lac operator was cloned into this plasmid using synthetic oligonucleotide linker by means of the EcoR I and Xba 1 restriction enzyme sites.

Linker 78 was made by annealing the oligonucleotides 7 and 8

Oligonucleotide 7
(SEQ ID NO 11)
5'AATTATCTCTGGCGGTGTTGACATAAATACCACTGGCGGTGATACTG
AGCGGAATTGTGAGCGCTCACAATTCCCCA Oligonucleotide 8
(SEQ ID NO 12)
5'CTAGTGGGAATTGTGAGCGCTCACAATTCCGCTCAGTATCACCGCC
AGTGGTATTTATGTCAACACCGCCAGAGAT The linker was then ligated to plasmid pZT7#2.0 and transformed into cloning host strain XL-1 Blue MR (Stratagene) as an Xba 1/EcoR I fragment. Initial screening of transformants was by restriction digestion using Nco 1. The sequence was confirmed by sequencing. The resultant plasmid was named pAVE029.

A human TNFα gene was cloned into this plasmid as an Nde I/Xho I fragment to generate pAVE027.

Vectors pAVE043 and pAVE044

The starting vector for the generation of pAVE043 was pAVE012. A tac promoter cassette was cloned into pAVE012 by annealing oligonucleotides 17 and 18:

Oligonucleotide 17
(SEQ ID NO 37)
5'AATTTTCTGAAATGAGCTGTTGACAATTAATCATCGGCTCGTATAAT
GTGTGGAATTGTGAGCGCTCACAATTCCCCA Oligonucleotide 18
(SEQ ID NO 38)
5'CTAGTGGGGAATTGTGAGCGCTCACAATTCCACACATTATACGAGCC
GATGATTAATTGTCAACAGCTCATTTCAGAA the annealed oligonucleotides being ligated to plasmid pAVE012 and transformed into cloning host strain XL-1 Blue MR (Stratagene) as an Xba 1/EcoR I fragment. Initial screening was by restriction digest of plasmid DNA. The sequence was then confirmed by sequencing. The resultant plasmid was named pAVE043.

A human TNFα gene was cloned into this plasmid as an Nde I/Xho I fragment to generate pAVE044.

Vectors pAVE034 and pAVE035

The starting vector for the generation of pAVE034 was pAVE012. A λpL promoter cassette was cloned into pAVE012 by annealing oligonucleotides 9 and 10:

```
Oligonucleotide 9
                                           (SEQ ID NO 39)
5'AATTCATCTCTGGCGGTGTTGACATAAATACCACTGGCGGTGATACT
GAGCGGAATTGTGAGCGCTCACAATTCCCCA Oligonucleotide 10
                                           (SEQ ID NO 40)
5'CTAGTGGGGAATTGTGAGCGCTCACAATTCCGCTCAGTATCACCGCC
AGTGGTATTTATGTCAACACCGCCAGAGATG
``` the annealed oligonucleotides being ligated to plasmid pAVE012 and transformed into cloning host strain XL-1 Blue MR (Stratagene) as an Xba 1/EcoR I fragment. Initial screening was by restriction digest of plasmid DNA. The sequence was then confirmed by sequencing. The resultant plasmid was named pAVE034.

A human TNFα gene was cloned into this plasmid as an Nde I/Xho I fragment to generate pAVE035.

Vector pAVE020 and pAVE021

The starting vector for the generation of pAVE020 was pAVE012. A λpL promoter cassette was cloned into pAVE012 by annealing oligonucleotides 7 and 8.

```
Oligonucleotide 7
                                           (SEQ ID NO 11)
5'AATTATCTCTGGCGGTGTTGACATAAATACCACTGGCGGTGATACTG
AGCGGAATTGTGAGCGCTCACAATTCCCCA Oligonucleotide 8
                                           (SEQ ID NO 12)
5'CTAGTGGGGAATTGTGAGCGCTCACAATTCCGCTCAGTATCACCGC
CAGTGGTATTTATGTCAACACCGCCAGAGAT
``` the annealed oligonucleotides being ligated to plasmid pAVE012 and transformed into cloning host strain XL-1 Blue MR (Stratagene) as an Xba 1/EcoR I fragment. Initial screening was by restriction digest of plasmid DNA. The sequence was then confirmed by sequencing. The resultant plasmid was named pAVE020.

A human TNFα gene was cloned into this plasmid as an Nde I/Xho I fragment to generate pAVE021.

Vectors pAVE016 and pAVE017

The starting vector for the generation of pAVE016 was pAVE012. A tac promoter cassette was cloned into pAVE012 by annealing oligonucleotides 15 and 16.

```
Oligonucleotide 15
                                           (SEQ ID NO 13)
5'AATTCCTGAAATGAGCTGTTGACAATTAATCATCGGCTCGTATAATG
TGTGGAATTGTGAGCGCTCACAATTCCCCA Oligonucleotide 16
                                           (SEQ ID NO 14)
5'CTAGTGGGGAATTGTGAGCGCTCACAATTCCACACATTATACGAGCC
GATGATTAATTGTCAACAGCTCATTTCAGG
``` the annealed oligonucleotides being ligated to plasmid pAVE012 and transformed into cloning host strain XL-1 Blue MR (Stratagene) as an Xba 1/EcoR I fragment. Initial screening was by restriction digest of plasmid DNA. The sequence was then confirmed by sequencing. The resultant plasmid was named pAVE016.

A human TNFα gene was cloned into this plasmid as an Nde I/Xho I fragment to generate pAVE017.

Vector pAVE049

The starting vector for the generation of pAVE049 was pAVE017. The tac promoter cassette was not altered. To increase the spacing between the two operators from 91 to 124 base pairs, an EcoR I linker was cloned in. This was made up of oligonucleotides 19 and 20.

```
Oligonucleotide 19
                                           (SEQ ID NO 15)
5'AATTCACCGGTGTACAGTCATGTACAACCGGTG Oligonucleotide 20
                                           (SEQ ID NO 16)
5'AATTCACCGGTTGTACATGACTGTACACCGGTG
```

Initial screening was by restriction digest of plasmid DNA. The sequence was then confirmed by sequencing. The resultant plasmid was named pAVE049.

Vector pAVE046

The starting vector for the generation of secretion vector pAVE046 was pAVE027. A D1.3 Fab expression cassette (FIG. 1, SEQ ID NO 17) was cloned as an Nde I-Bam HI fragment. Initial screening was by restriction digest of plasmid DNA. The sequence was then confirmed by sequencing. The resultant plasmid was named pAVE046.

TABLE 1

Summary of pAVE vectors

| Plasmid | Promoter | Operator System | Comments |
| --- | --- | --- | --- |
| pAVE041 | tac | Single native lac sequence | |
| pAVE017 | tac | Double perfect palindrome sequences (DPPS) | Operator spacing 91 base pairs (DPPS91) |
| pAVE040 | tac | Single perfect palindrome sequence (SPPS) | |
| pAVE049 | tac | Double perfect palindrome sequences | Operator spacing 124 base pairs (DPPS124) |
| pAVE013 | T7A3 | Double perfect palindrome sequences | Operator spacing 91 base pairs (DPPS91) |
| pAVE030 | T7A3 | Double perfect palindrome sequences | Operator spacing 92 base pairs (DPPS92) |
| pAVE031 | T7A3 | Single perfect palindrome sequence | |
| pAVE021 | λpL | Double perfect palindrome sequences | Operator spacing 91 base pairs (DPPS91) |
| pAVE035 | λpL | Double perfect palindrome sequences | Operator spacing 92 base pairs (DPPS92) |
| pAVE027 | λpL | Single perfect palindrome sequence | |
| pAVE046 | λpL | Single perfect palindrome sequence | Secretion Vector |

2. GENERATION OF RECOMBINANT STRAINS

*E. coli* strains W3110 (available from the American Type Culture Collection as strain ATCC27325) and BL21 (available from EMD Biosciences Inc, San Diego, USA) were transformed by electroporation with the plasmids as described in Table 2 below. The resultant recombinant strains were purified and maintained in glycerol stocks at −80° C.

TABLE 2

Recombinant strains constructed

| Host | Plasmid | Description (protein:promoter:operator system) | Recombinant Designation No |
|---|---|---|---|
| ATCC27325 | pAVE013 | TNFα:T7A3:DPPS91 | CLD018 |
| ATCC27325 | pAVE030 | TNFα:T7A3:DPPS92 | CLD026 |
| ATCC27325 | pAVE031 | TNFα:T7A3:SPPS | CLD032 |
| ATCC27325 | pAVE041 | TNFα:tac:single native lacO | CLD043 |
| ATCC27325 | pAVE017 | TNFα:tac:DPPS91 | CLD019 |
| ATCC27325 | pAVE040 | TNFα:tac:SPPS | CLD042 |
| ATCC27325 | pAVE049 | TNFα:tac:DPPS124 | CLD050 |
| ATCC27325 | pAVE021 | TNFα:λpL:DPPS91 | CLD021 |
| ATCC27325 | pAVE035 | TNFα:λpL:DPPS92 | CLD038 |
| ATCC27325 | pAVE027 | TNFα:λpL:SPPS | CLD030 |
| BL21 | pAVE013 | TNFα:T7A3:DPPS91 | CLD035 |
| BL21 | pAVE030 | TNFα:T7A3:DPPS92 | CLD028 |
| ATCC27325 | pAVE046 | D1.3 Fab:λpL:SPPS | CLD048 |

Comparison 1

The starting vector for the generation of a plasmid with the T7A3 promoter without any operator was pZT7#2.0. A T7A3 promoter was cloned into this plasmid using synthetic oligonucleotide Tinker by means of the EcoR I and Xba 1 restriction enzyme sites.

Linker 2122 was made by annealing the oligonucleotides 21 and 22

```
Oligonucleotide 21
                                    (SEQ ID NO 18)
5'AATTCGAAACAAAACGGTTGACAACATGAAGTAAACACGGTACGATG
TACCACATGAAACGACAGTGAGTCA Oligonucleotide 22
                                    (SEQ ID NO 19)
5'CTAGTGACTCACTGTCGTTTCATGTGGTACCTCGTACCGTGTTTACT
TCATGTTGTCAACCGTTTTGTTTCG
```

The linker was then ligated to plasmid pZT7#2.0 and transformed into cloning host strain XL-1 Blue MR (Stratagene) as an Xba I/EcoR I fragment. Initial screening was by restriction digest of plasmid DNA. The sequence was then confirmed by sequencing. Eighty-two clones were screened by restriction digest and sequencing.

No clones were identified with the correct T7A3 promoter sequence (all contained mutations in the sequence). This suggests that construction of plasmids containing this powerful constitutive promoter is problematic.

Comparison 2

The starting vector for the generation of a plasmid with the T7A3 promoter under the control of a single native Lac operator sequence was pZT7#2.0. A T7A3 promoter and native Lac operator (LacO) sequence was cloned into this plasmid using synthetic oligonucleotide Tinker by means of the EcoR I and Xba 1 restriction enzyme sites.

Linker 2324 was made by annealing the oligonucleotides 23 and 24

```
Oligonucleotide 23
                                    (SEQ ID NO 20)
5'AATTCGAAACAAAACGGTTGACAACATGAAGTAAACACGGTACGATGT
ACCGGAATTGTGAGCGGATAACAATTCCCCA Oligonucleotide 24
                                    (SEQ ID NO 21)
5'CTAGTGGGGAATTGTTATCCGCTCACAATTCCGGTACATCGTACCGTG
TTTACTTCATGTTGTCAACCGTTTTGTTTCG
```

The linker was then ligated to plasmid pZT7#2.0 and transformed into cloning host strain XL-1 Blue MR (Stratagene) as an Xba I/EcoR I fragment. Initial screening was by restriction digest of plasmid DNA. The sequence was then confirmed by sequencing. Ninety-four clones were screened by restriction digestion and sequencing. Again no clones were identified with the correct sequence. However, one clone was found to have a near intact sequence. This clone contained an additional 'G' in the sequence approximately at position −37. It is difficult to assign exact position of the mutation since the expected sequence contains -GG- in this region. Human TNFα gene was cloned into the plasmid with the near intact sequence as an Nde I/Xho I fragment. Twenty colonies from the cloning host strain XL-Blue MR (Stratagene) were screened. One was positive clone with no mutations (other than the additional 'G' described above). This plasmid was transformed into a production host (ATCC27325) and the plasmid re-sequenced.

This indicated that the plasmid contained gross mutations in both the T7A3 promoter and the human TNFα sequences indicating that the use of the T7A3 promoter, even under the control of the native lac operator sequence, results in plasmid instability.

Example 3

A vial of CLD032 was removed from the −80° C. freezer and allowed to thaw. 10 μl of the thawed glycerol stock was inoculated into 5 ml Luria Broth (LB, 5 g/L yeast extract (Oxoid), 10 g/L tryptone (Oxoid), and 5 g/L sodium chloride) supplemented with tetracycline (10 μg/ml) and glucose (1 g/L). This was incubated at 37° C. in an orbital shaker for 16 h. 500 μl of this culture was then used to inoculate two 250 ml Erlenmeyer flasks containing 50 ml of Luria Broth (composition as described above). The flasks were incubated at 37° C., at 200 rpm in an orbital shaker. Growth was monitored until $OD_{600}$=0.5-0.7. At this point one flask was induced with IPTG (isopropyl-β.-D-1-thiogalactopyranoside) to a final concentration 0.05 mM whilst the second flask was left un-induced to monitor basal expression. The incubation was continued, under the conditions described above, during which samples were taken for measurement of growth, accumulation of hTNFα within the bacterial cells. The accumulation level of hTNFα was determined using densitometry scanning of Colloidal Blue stained SDS-PAGE gels of whole cell lysates of the sampled bacteria. The results are summarised below in Table 3.

TABLE 3

| Time (hours) | Accumulation Level of hTNFα (% TCP*) |
|---|---|
| 3 | 2 |
| 4 | 18 |
| 6 | 25 |
| 8 | 33 |
| 24 | 42 |
| 24 (basal, no IPTG) | 13 |

*TCP = Total Cell Protein

Taken together the data presented in Comparisons 1 and 2, and Example 3, show that effective control of the powerful T7A3 promoter was surprisingly achieved using a single perfect palindrome operator sequence. This was totally un-expected given that the use of the single native operator (Comparison 2) did not provide sufficient basal control to allow a stable recombinant production strain to be established. High product accumulation levels were achieved with the single perfect palindrome control system using relatively low concentration of inducer for induction. Although basal expression (in the absence of inducer) was observed it was evident only after significantly extended incubation (24 h).

Example 4

Vials of CLD018 was removed from the −80° C. freezer and allowed to thaw. 10 µl of the thawed glycerol stock was inoculated into 5 ml Luria Broth (LB, 5 g/L yeast extract (Oxoid), 10 g/L tryptone (Oxoid), and 5 g/L sodium chloride) supplemented with tetracycline (10 µg/ml) and glucose (1 g/L). The seed culture was incubated at 37° C. in an orbital shaker for 16 h. 500 µl of the seed culture was then used to inoculate 250 ml Erlenmeyer flasks containing 50 ml of Luria Broth (composition as described above). The flasks were incubated at 37° C., at 200 rpm in an orbital shaker. Growth was monitored until $OD_{600}$=0.5-0.7. At this point flasks were induced with IPTG (isopropyl-.β.-D-1-thiogalactopyranoside) to a final concentration 0.05 mM and 1 mM. A flask was also left un-induced and the incubation of the flasks continued, under the conditions described above, during which samples were taken for measurement of growth, accumulation of hTNFα within the bacterial cells. The accumulation level of hTNFα was determined using densitometry scanning of Colloidal Blue stained SDS-PAGE gels of whole cell lysates of the sampled bacteria. The results are summarised below in Table 4.

TABLE 4

| | Accumulation Level of hTNFα (% TCP) |
|---|---|
| 0.05 mM IPTG Time (hours) | |
| 3 | 2 |
| 4 | 5 |
| 6 | 8 |
| 8 | 13 |
| 24 | 19 |
| 24 (basal, no IPTG) | Not detected |
| 1 mM IPTG Time (hours) | |
| 5 | 7 |
| 6 | 12 |
| 8 | 19 |
| 24 | 26 |

This data demonstrated that further control of the powerful T7A3 promoter could be realised using two perfect palindrome operator sequences spaced at 91 bp apart. Basal expression (in the absence of inducer) has been reduced significantly from that achieved using a single perfect palindrome operator to control repression. The control of basal expression achieved using the dual perfect palindrome sequences was un-expected when compared to the T7 system of U.S. Pat. No. 6,537,779 where control of basal expression requires two different control elements. In this example control of basal expression was achieved in a high background of E. coli RNA polymerase.

Example 5

Vials of CLD026 was removed from the −80° C. freezer and allowed to thaw. 10 µl of the thawed glycerol stock was inoculated into 5 ml Luria Broth (LB, 5 g/L yeast extract (Oxoid), 10 g/L tryptone (Oxoid), and 5 g/L sodium chloride) supplemented with tetracycline (10 µg/ml) and glucose (1 g/L). This was incubated at 37° C. in an orbital shaker for 16 h. 500 µl of this culture was then used to inoculate 250 ml Erlenmeyer flasks containing 50 ml of Luria Broth (composition as described above). The flasks were incubated at 37° C., at 200 rpm in an orbital shaker. Growth was monitored until $OD_{600}$=0.5-0.7. At this point flasks were induced with IPTG (isopropyl-.β.-D-1-thiogalactopyranoside) to a final concentration 0.05 mM and 0.005 mM. A flask was also left un-induced and the incubation continued, under the conditions described above, during which samples were taken for measurement of growth, accumulation of hTNFα within the bacterial cells. The accumulation level of hTNFα was determined using densitometry scanning of Colloidal Blue stained SDS-PAGE gels of whole cell lysates of the sampled bacteria. The results are summarised below in Table 5.

TABLE 5

| | Accumulation Level of hTNFα (% TCP) |
|---|---|
| 0.005 mM IPTG induction Time (hours) | |
| 8 | 15 |
| 24 (basal, no IPTG) | Not detected |
| 0.05 mM IPTG induction Time (hours) | |
| 8 | 17 |

The results demonstrated that changing the spacing between the two perfect palindrome operator sequences by 1 bp (from 91 to 92 bp) did not adversely influence performance both in terms of basal expression and final accumulation level achieved.

Unexpectedly, reducing the IPTG concentration 10 fold (from 0.05 mM to 0.005 mM) did not significantly reduce induced productivity.

Example 6

Vials of CLD042 and CLD043 were removed from the −80° C. freezer and allowed to thaw. 10 µl of each of the thawed glycerol stock was inoculated separately into each of 2×5 ml Luria Broth (LB, 5 g/L yeast extract (Oxoid), 10 g/L tryptone (Oxoid), and 5 g/L sodium chloride) supplemented with tetracycline (10 µg/ml) and glucose (1 g/L). These were incubated at 37° C. in an orbital shaker for 16 h. 500 µl of these cultures were then used to separately inoculate 250 ml Erlenmeyer flasks containing 50 ml of Luria Broth (composition as described above). The flasks were incubated at 37° C., at 200 rpm in an orbital shaker. Growth was monitored until $OD_{600}$=0.5-0.7. At this point flasks were induced with IPTG (isopropyl-.β.-D-1-thiogalactopyranoside) to a final concentration 0.5 mM. Flasks containing a culture of each strain were also left un-induced and the incubation continued, under the conditions described above, during which samples were taken for measurement of growth, accumulation of hTNFα within the bacterial cells. The accumulation level of hTNFα was determined using densitometry scanning of Colloidal Blue stained SDS-PAGE gels of whole cell lysates of the sampled bacteria. The basal accumulation level of hTNFα in the un-induced cultures of CLD042 and CLD043 after 20 hours incubation was compared by Western blot analysis (using anti-hTNFα antibody) following SDS-PAGE of the sampled bacteria. The blots were scanned and the data normalised to enable comparison. The results are summarised below in Table 6.

TABLE 6

| Time (hours) | Accumulation Level of hTNFα (% TCP) |
|---|---|
| CLD043: tac promoter, single native lac operator - 0.5 mM IPTG induction | |
| 3 | 6 |
| 12 | 23 |
| 20 | 25 |
| Western Blot: scan intensity* | |
| 20 (Basal, no IPTG) | 1 |
| CLD042: tac promoter, single perfect palindrome operator - 0.5 mM IPTG induction | |
| 3 | 2 |
| 12 | 18 |
| 20 | 21 |
| Western Blot: scan intensity* | |
| 20 (Basal, no IPTG) | 0.25 |

*= scan of hTNFα band on Western blot. Intensity scan data for CLD042 normalised against the intensity scan data for CLD043.

The results demonstrated that the single perfect palindrome operator sequence can be used to reduce basal expression (in the absence of inducer) four fold without adversely influencing the induced productivity of the tac promoter system.

Example 7

A vial of CLD019 was removed from the −80° C. freezer and allowed to thaw. 10 μl of the thawed glycerol stock was inoculated into 5 ml Luria Broth (LB, 5 g/L yeast extract (Oxoid), 10 g/L tryptone (Oxoid), and 5 g/L sodium chloride) supplemented with tetracycline (10 μg/ml) and glucose (1 g/L). This was incubated at 37° C. in an orbital shaker for 16 h. 500 μl of this culture was then used to inoculate 250 ml Erlenmeyer flasks containing 50 ml of Luria Broth (composition as described above). The flasks were incubated at 37° C., at 200 rpm in an orbital shaker. Growth was monitored until $OD_{600}$=0.5-0.7. At this point the flasks were induced with IPTG thiogalactopyranoside) to a final concentration 0.5 mM, 0.1 mM, 0.05 mM and 0.005 mM. A flask was also left un-induced and the incubation continued, under the conditions described above, during which samples were taken for measurement of growth, and accumulation of hTNFα within the bacterial cells. The accumulation level of hTNFα was determined using densitometry scanning of Colloidal Blue stained SDS-PAGE gels of whole cell lysates of the sampled bacteria. The results are presented in FIG. 2.

The data presented in FIG. 2 demonstrated that the combination of the tac promoter with dual perfect palindrome operator sequences lead to a system in which the expression rate can be modulated directly by the concentration of IPTG used for induction. Such systems may be exploited to modulate expression of heterologous proteins, for example, to maximise accumulation of proteins in a soluble form or to circumvent the problem of the deleterious effect that heterologous protein secretion can have on the growth and productivity of recombinant cells.

Example 8

A vial of CLD030 was removed from the −80° C. freezer and allowed to thaw. 10 μl of the thawed glycerol stock was inoculated into 5 ml Luria Broth (LB, 5 g/L yeast extract (Oxoid), 10 g/L tryptone (Oxoid), and 5 g/L sodium chloride) supplemented with tetracycline (10 μg/ml) and glucose (1 g/L). This was incubated at 37° C. in an orbital shaker for 16 h. 500 μl of this culture was then used to inoculate 250 ml Erlenmeyer flasks containing 50 ml of Luria Broth (composition as described above). The flasks were incubated at 37° C., at 200 rpm in an orbital shaker. Growth was monitored until $OD_{600}$=0.5-0.7. At this point a flask was induced with IPTG (isopropyl-β.-D-1-thiogalactopyranoside) to a final concentration 0.05 mM whilst the other flask was left un-induced and the incubation continued, under the conditions described above, during which samples were taken for measurement of growth, accumulation of hTNFα within the bacterial cells. The accumulation level of hTNFα was determined using densitometry scanning of Colloidal Blue stained SDS-PAGE gels of whole cell lysates of the sampled bacteria. The results are summarised below in Table 7.

TABLE 7

| Time (hours) | Accumulation Level of hTNFα (% TCP) |
|---|---|
| 4 | 2 |
| 6 | 5 |
| 8 | 9 |
| 24 | 12 |
| 24 (basal, no IPTG) | Not detected |

The data presented in Table 7 clearly show that control of the very powerful λpL promoter can be surprisingly achieved using a single perfect palindrome operator sequence. High product accumulation levels can be achieved using the single perfect palindrome control system.

Example 9

Figure 3:
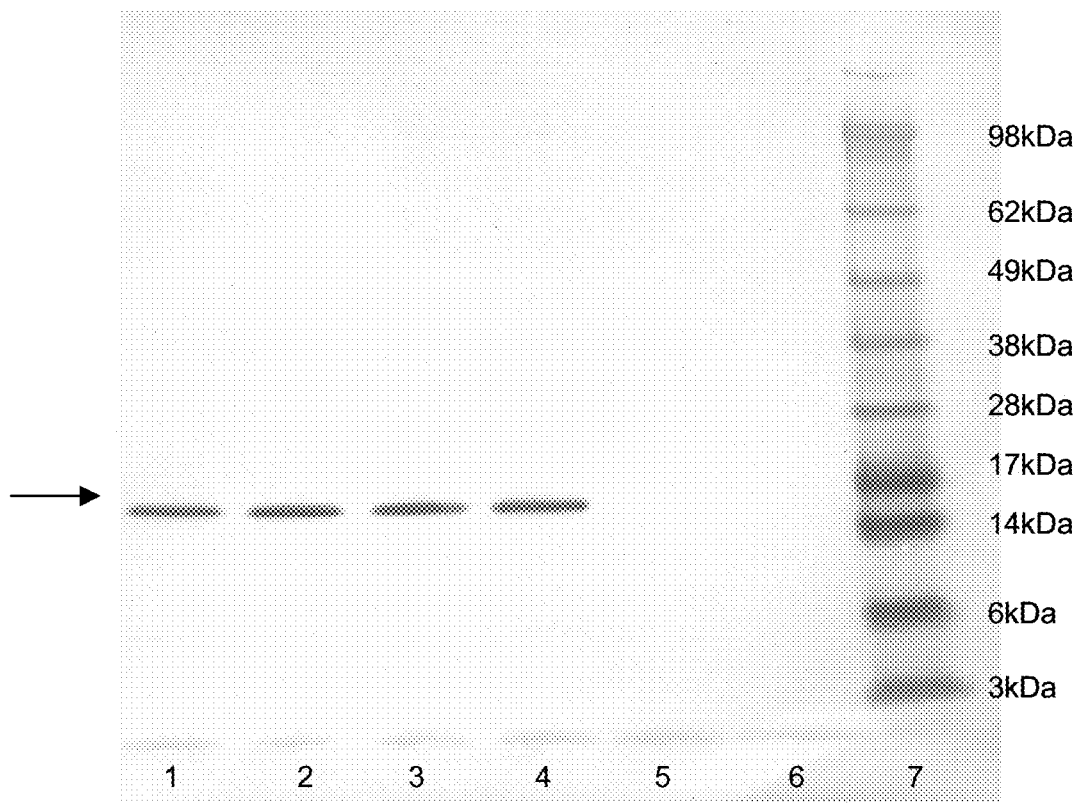
FIG. 3 shows Western blot analysis for strain CLD038 according to Example 9.

Vials of CLD021 and CLD038 were removed from the −80° C. freezer and allowed to thaw. 10 μl of each of the thawed glycerol stock was inoculated separately into 5 ml Luria Broth (LB, 5 g/L yeast extract (Oxoid), 10 g/L tryptone (Oxoid), and 5 g/L sodium chloride) supplemented with tetracycline (10 μg/ml) and glucose (1 g/L). These were incubated at 37° C. in an orbital shaker for 16 h. 500 μl of this culture was then used to inoculate 250 ml Erlenmeyer flasks containing 50 ml of Luria Broth (composition as described above). The flasks were incubated at 37° C., at 200 rpm in an orbital shaker. Growth was monitored until $OD_{600}$=0.5-0.7. At this point a flask was induced with IPTG (isopropyl-β.-D-1-thiogalactopyranoside) to a final concentration 1 mM whilst a second flask was left un-induced and the incubation continued, under the conditions described above, during which samples were taken for measurement of growth, accumulation of hTNFα within the bacterial cells. The accumulation of hTNFα was determined using Colloidal Blue stained SDS-PAGE gels and Western blot analysis (using anti-hTNFα antibody) following SDS-PAGE of whole cell lysates of the sampled bacteria. The data are summarised in Table 8. The Western blot analysis for strain CLD038 is presented in FIG. 3.

TABLE 8

| Analysis | hTNFα Accumulation - CLD021 (λpL:DPPS91) | hTNFα Accumulation - CLD038 (λpL:DPPS92) |
|---|---|---|
| Colloidal Blue SDS-PAGE (post IPTG induction) | Not detected | Not detected |
| Western blot (post IPTG induction) | Positive | Positive (see FIG. 2) |
| Colloidal Blue SDS-PAGE (Basal no IPTG induction, 24 h) | Not detected | Not detected |
| Western blot (Basal no IPTG induction, 24 h) | Not detected | Not detected |

These results demonstrated that the combination of dual perfect palindrome operator sequences with the λpL promoter with either the 91 bp or 92 bp spacing resulted in very tight repression. Western blots indicate that no basal expression of the target protein was detected. On induction low-level expression level was achieved. These results were totally unexpected given that the λpL promoter is an extremely powerful promoter. Such a system may, for example, be used to direct the expression of proteins of high toxicity to the host cell. It can be used when controlled expression is advantageous, for example, for the expression and insertion of membrane proteins.

Example 10

Vials of CLD028 and CLD035 were removed from the −80° C. freezer and allowed to thaw. 10 μl of each of the thawed glycerol stock was inoculated separately into each of 2×5 ml Luria Broth (LB, 5 g/L yeast extract (Oxoid), 10 g/L tryptone (Oxoid), and 5 g/L sodium chloride) supplemented with tetracycline (10 μg/ml) and glucose (1 g/L). These were incubated at 37° C. in an orbital shaker for 16 h. 500 μl of these cultures were then used to separately inoculate 250 ml Erlenmeyer flasks containing 50 ml of Luria Broth (composition as described above). The flasks were incubated at 37° C., at 200 rpm in an orbital shaker. Growth was monitored until $OD_{600}$=0.5-0.7. At this point flasks were induced with IPTG (isopropyl-.β.-D-1-thiogalactopyranoside) to a final concentration 1 mM and the incubation continued, under the conditions described above, during which samples were taken for measurement of growth, accumulation of hTNFα within the bacterial cells. The accumulation level of hTNFα was determined using densitometry scanning of Colloidal Blue stained SDS-PAGE gels of whole cell lysates of the sampled bacteria. The results are summarised below in Table 9.

TABLE 9

| Time (hours) post IPTG induction | Accumulation Level of hTNFα (% TCP) |
|---|---|
| CLD035: T7A3 promoter, dual perfect palindrome operators with 91 bp spacing | |
| 2 | 7 |
| 4 | 14 |
| 20 | 27 |
| CLD028: T7A3 promoter, dual perfect palindrome operators with 92 bp spacing | |
| 2 | 10 |
| 4 | 15 |
| 20 | 23 |

These data taken together with the data presented in Examples 4 and 5 previously indicated that both E. coli K-12 and B strains can be used.

Example 11

Fermentation inocula were raised by adding 200 μl of glycerol stock of each of the strains described below to a 2.0 L baffled shake flask containing 200 mL of Luria Broth (LB, 5 g/L yeast extract (Oxoid), 10 g/L tryptone (Oxoid), and 5 g/L sodium chloride) supplemented with 15 μg/ml of tetracycline. Inocula were grown for 12 h at 37° C. in a shaker-incubator with an agitation of 250 rpm. 200 ml shake flask inoculum was used to inoculate a 15 L working volume fermenter containing 10 L of batch growth medium. Fermentations were carried out under the operating conditions described below. Temperature was controlled at 37° C. and pH at 6.8, controlled by automatic addition of 35% (w/v) ammonium hydroxide. The dissolved oxygen tension (dOT) set point was 30% of air saturation and was controlled by automatic adjustment of the fermenter stirrer speed, from a minimum of 250 rpm up to a maximum of 1500 rpm, and automatic supplementation of oxygen to the inlet gas stream. Airflow to the fermenter vessel was 10 L/min throughout. Pressure in the fermenter was maintained between 50 and 200 mbar.

Fermentations were performed in batch mode until depletion of the carbon source (i.e. glycerol) which occurred ca. 10 h post inoculation and was characterized by a sharp rise in dOT. Fed-batch fermentation was initiated at the point of carbon source exhaustion by the addition of a glycerol/magnesium chloride feed at a feed rate of 11 g of glycerol per L of medium per h. Induction was carried out by addition of IPTG to a final concentration of 0.5 mM once the biomass level in the fermentation reached $OD_{600}$=50-60. The fed-batch phase was continued for 12 h post induction. Samples were taken to determine biomass level ($OD_{600}$) and hTNFα accumulation (% TCP)/hTNFα titre (g/L) at harvest (Colloidal Blue stained SDS-PAGE gels).

The composition of the batch growth medium is provided in Table 10.

TABLE 10

| Component | Final concentration [g/L], mg/L] and [ml/L] of purified water |
|---|---|
| $(NH_4)_2SO_4$ | 14.0 |
| Glycerol | 35.0 |
| Yeast extract (Becton Dickinson) | 20.0 |
| $KH_2PO_4$ | 2.0 |
| $K_2HPO_4$ | 16.5 |
| Citric acid | 7.5 |
| $MgSO_4 \cdot 7H_2O$ | 2.47 |
| $H_3PO_4$ | 1.5 ml/L |
| $CaCl_2 \cdot 2H_2O$ | 0.294 |

TABLE 10-continued

| Component | Final concentration [g/L], mg/L] and [ml/L] of purified water |
|---|---|
| Antifoam AF204 | 0.2 ml/L |
| Tetracycline | 15 mg/L |
| $FeSO_4 \cdot 7H_2O$ | 114 mg/L |
| $ZnSO_4 \cdot 7H_2O$ | 29 mg/L |
| $MnSO_4 \cdot H_2O$ | 17 mg/L |
| $Na_2MoO_4 \cdot 2H_2O$ | 9 mg/L |
| $CuSO_4 \cdot 5H_2O$ | 4 mg/L |
| $H_3 \cdot BO_3$ | 12 mg/L |

The composition of the glycerol/magnesium chloride feed is provided in Table 11.

TABLE 11

| Component of Feed | Amount required [g/L] of purified water |
|---|---|
| Glycerol | 714 |
| $MgSO_4 \cdot 7H_2O$ | 7.4 |

Figure 4:
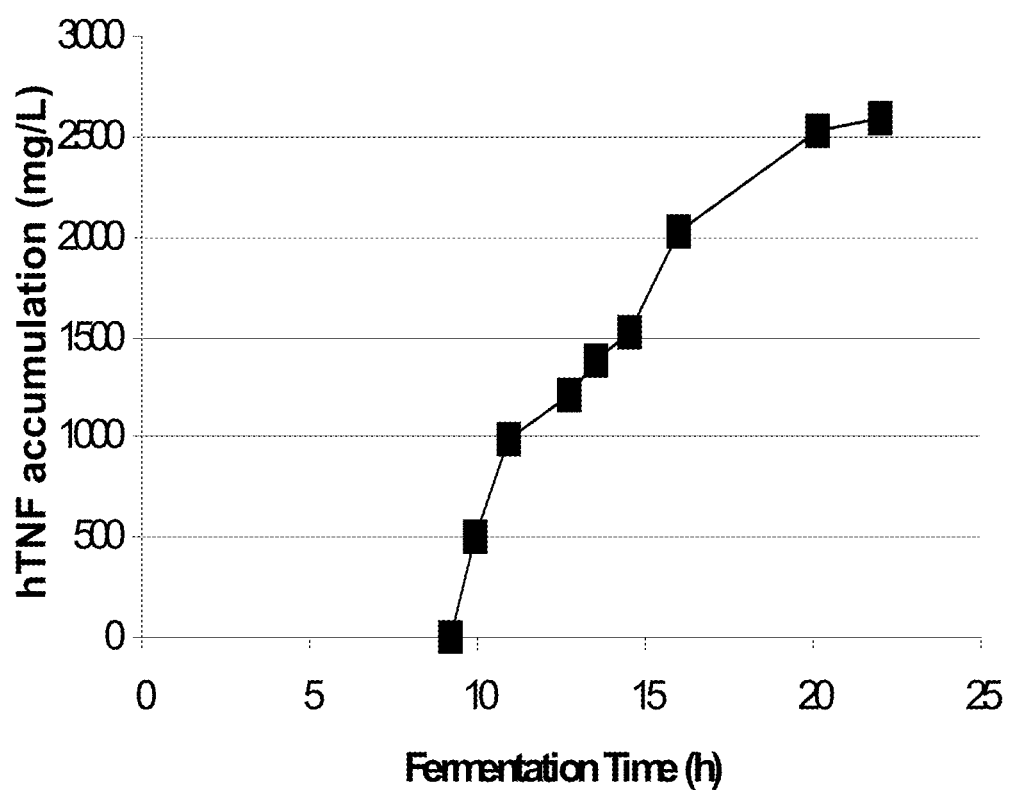
FIG. 4 shows the hTNFα productivity profile for Strain CLD030 according to Example 11.

The results are summarised in Table 12. The hTNFα productivity profile for Strain CLD030 is presented in FIG. 4.

TABLE 12

| Strain | Expression vector description | OD600 at harvest | hTNFα accumulation (% TCP) at harvest | hTNFα titre (mg/L) at harvest |
|---|---|---|---|---|
| CLD018 | T7A3 promoter, dual perfect palindrome with 91 bp spacing | 147 | 29 | 8400 |
| CLD026 | T7A3 promoter, dual perfect palindrome with 92 bp spacing | 204 | 34 | 11400 |
| CLD032 | T7A3 promoter, single perfect palindrome sequence | 194 | 41 | 12500 |
| CLD019 | tac promoter, dual perfect palindrome sequence with 91 bp spacing | 196 | 22 | 8300 |
| CLD030 | λpL promoter with single perfect palindrome sequence | 167 | 7 | 2600 |

The data clearly demonstrate the utility of the systems for the manufacture of heterologous proteins. High product titres were achieved using a simple generic un-optimised fermentation and induction processes. The control characteristics of plasmid pAVE027, as demonstrated by productivity profile exemplified in FIG. 4, can be exploited to maximize the production of heterologous proteins, particularly proteins that require control of expression to maximize secretion.

Example 12

A vial of CLD050 was removed from the −80° C. freezer and allowed to thaw. 10 μl of the thawed glycerol stock was inoculated into 5 ml Luria Broth (LB, 5 g/L yeast extract (Oxoid), 10 g/L tryptone (Oxoid), and 5 g/L sodium chloride) supplemented with tetracycline (10 μg/ml) and glucose (1 g/L). This was incubated at 37° C. in an orbital shaker for 16 h. 500 μl of this culture was then used to inoculate 250 ml Erlenmeyer flasks containing 50 ml of Luria Broth (composition as described above). The flasks were incubated at 37° C., at 200 rpm in an orbital shaker. Growth was monitored until $OD_{600}$=0.5-0.7. At this point a flask was induced with IPTG (isopropyl-.β.-D-1-thiogalactopyranoside) to a final concentration 0.05 mM whilst another flask was left uninduced and the incubation continued, under the conditions described above, during which samples were taken for measurement of growth, accumulation of hTNFα within the bacterial cells. The accumulation level of hTNFα was determined using densitometry scanning of Colloidal Blue stained SDS-PAGE gels of whole cell lysates of the sampled bacteria. The results are summarised below in Table 13.

TABLE 13

| Time post induction (hours) | Accumulation Level of hTNFα (% TCP) |
|---|---|
| 4 | 16 |
| 24 (basal, no IPTG) | Not detected |

Surprisingly the dual perfect palindrome operator sequence worked when the spacing was increased. The spacing of the dual perfect palindrome can be altered, for example, to achieve effective control of other promoters.

Example 13

A vial of CLD048 was removed from the −80° C. freezer and allowed to thaw. 10 μl of the thawed glycerol stock was inoculated into 5 ml Luria Broth (LB, 5 g/L yeast extract (Oxoid), 10 g/L tryptone (Oxoid), and 5 g/L sodium chloride) supplemented with tetracycline (10 μg/ml) and glucose (1 g/L). This was incubated at 37° C. in an orbital shaker for 16 h. 500 μl of this culture was then used to inoculate a 250 ml Erlenmeyer flask containing 50 ml of Luria Broth (composition as described above). The flask was incubated at 37° C., at 200 rpm in an orbital shaker. Growth was monitored until $OD_{600}$=0.5-0.7. At this point the flask was induced with IPTG (isopropyl-.β.-D-1-thiogalactopyranoside) to a final concentration of 0.1 mM and the incubation continued, under the conditions described above for a further 2 h. The cells and residual cell free growth medium were then harvested. The harvested cells were further subjected to osmotic shock cell fractionation to isolate the cellular fraction containing proteins that had partitioned in the soluble E. coli periplasmic fraction. The accumulation of biologically active D1.3 Fab in the soluble periplasmic extract and residual growth medium was estimated by determining the binding of D1.3 Fab to lysozyme (antigen) in an ELISA assay by reference to a standard curve prepared with purified active D1.3 Fab. The accumulation of biologically active D1.3 Fab in the periplasm of E. coli and in the residual growth medium (due to leakage of material from the periplasm to the growth medium) is presented in Table 14. The accumulation of D1.3 Fab in the periplasm and residual growth medium was normalised as "μg active material per litre of culture per unit of biomass ($OD_{600}$).

TABLE 14

| Fraction | Biologically active D1.3 Fab (μg/L culture/OD) |
|---|---|
| Residual growth medium | 460 |
| Periplasm | 4020 |
| Total (residual growth medium + periplasm) | 4480 |

The utility of the control provided by this system to enable high level secretion of heterologous proteins particularly those requiring complex disulphide bond formation is clearly exemplified by the secretion and accumulation of high levels of biologically active D1.3 Fab in the periplasm of E. coli. Additionally, it will be evident to those skilled in the art how fed-batch fermentation (for example, as described previously in Example 11 or below in Example 14) can be used to manufacture such proteins at high yield.

Example 14

The fermentation process described in Example 11 was repeated using CLD048. Induction was carried out by addition of IPTG to a final concentration of 0.15 mM once the biomass level in the fermentation reached $OD_{600}$=ca. 50. The fed-batch phase was continued for 35-45 h post induction. The cells and residual cell free growth medium were then harvested. The harvested cells were further subjected to osmotic shock cell fractionation to isolate the cellular fraction containing proteins that had partitioned in the soluble E. coli periplasmic fraction. The accumulation of biologically active D1.3 Fab in the soluble periplasmic extract and residual growth medium was estimated by determining the binding of D1.3 Fab to lysoszyme (antigen) in an ELISA assay by reference to a standard curve prepared with purified active D1.3 Fab. The accumulation of D1.3 Fab in the periplasm and residual growth medium was normalised as "mg active material per litre of culture".

The accumulation of biologically active D1.3 Fab in the periplasm of E. coli and in the residual growth medium (due to leakage of material from the periplasm to the growth medium) is presented in Table 15.

TABLE 15

| Fraction | Biologically active D1.3 Fab (mg/L culture) |
| --- | --- |
| Residual growth medium | 525 |
| Periplasm | 57 |
| Total (residual growth medium + periplasm) | 582 |

High level secretion of biologically active D1.3 Fab is demonstrated using the expression system.

Example 15

A synthetic bispecific single chain tetravalent diabody (bsctDb) was designed, in which the variable light and variable heavy regions from D1.3 (anti-lysozyme) and A5B7 (anti-CEA (carcinoembryonic antigen)), were linked on a single polypeptide chain. The DNA sequence for this molecule is shown in FIG. 5 (SEQ ID NO 22). This was cloned as an Nde I/Not I fragment into pAVE046 which had been digested with Nde I and Not I. Recombinant plasmids were screened by restriction digest and confirmed by sequencing. The resultant plasmid was named pAVE078. pAVE078 was transformed into E. coli W3110 to make CLD073, which was purified and maintained in glycerol stocks at −80° C.

A vial of CLD0073 was removed from the −80° C. freezer and allowed to thaw. 10 µl of the thawed glycerol stock was inoculated into 5 ml Luria Broth (LB, 5 g/L yeast extract (Oxoid), 10 g/L tryptone (Oxoid), and 5 g/L sodium chloride) supplemented with tetracycline (10 µg/ml) and glucose (1 g/L). This was incubated at 37° C. in an orbital shaker for 16 h. 500 µl of this culture was then used to inoculate two 250 ml Erlenmeyer flasks containing 50 ml of Luria Broth (composition as described above). The flasks were incubated at 37° C., at 200 rpm in an orbital shaker. Growth was monitored until $OD_{600}$=0.5-0.7. At this point the flasks were induced with IPTG to a final concentration of either 0.5 mM or 0.1 mM and the incubation continued, under the conditions described above for a further 20 hours. The cells and residual cell free growth medium were then harvested. The harvested cells were further subjected to osmotic shock cell fractionation to isolate the cellular fraction containing proteins that had partitioned in the soluble E. coli periplasmic fraction. The expression, secretion, folding and accumulation of biologically active D1.3-A5B7 bsctDb in the periplasmic extract and residual growth medium was estimated by determining the inhibition of binding of an anti-CEA monoclonal antibody to CEA (antigen) in a competitive ELISA assay and by the binding of an anti-lysozyme Fab antibody fragment to lysozyme (antigen) in a competitive ELISA assay.

The data obtained indicated that the majority of D1.3-A5B7 bsctDb partitioned in the residual growth medium (leakage from the periplasm) at the end of the induction. This data (binding of bsctDb in competitive ELISA) is shown in Table 16. The data obtained demonstrates that the residual growth medium sample from the culture induced with 0.5 mM IPTG completely inhibits the binding of both the anti-CEA and anti-lysozyme antibodies in the competition ELISA assays. The residual growth medium sample from the culture induced with 0.1 mM IPTG shows a reduced level of inhibition indicating a lower accumulation level of biologically active D1.3-A5B7 bsctDb in this sample.

TABLE 16

| Sample | % Inhibition in CEA Competition ELISA | % Inhibition in D1.3 Competition ELISA |
| --- | --- | --- |
| Control (No D1.3-A5B7 bsctDb) | None | None |
| Supernatant from culture induced with 0.5 mM IPTG | 100 | 100 |
| Supernatant from culture induced with 0.1 mM IPTG | Partial | Partial |

Using the new expression system it is possible to produce complex multi-chain heterologous proteins which have been difficult to produce using E. coli. This has been exemplified by demonstrating that bispecific single chain tetravalent diabodies in a biologically active form can be produced in E. coli using the new expression system. This further exemplifies the utility of the expression system.

Example 16

The glutathione-S-transferase-3C proteinase fusion (GST-3C) gene was cloned as an Nde I/Xho I fragment into pAVE011 digested with Nde I and Xho I. The sequence of the insert is shown in FIG. 6 (SEQ ID NO 23). Recombinant plasmids were screened by restriction digest and confirmed by sequencing. The resultant plasmid was named pAVE052. pAVE052 was transformed into E. coli BL21 to make CLD054, which was purified and maintained in glycerol stocks at −80° C.

The human Interferon α2 (IFNα2) gene was cloned as an Nde I/Xho I fragment into pAVE011 digested with Nde I and Xho I. The DNA sequence of the insert is shown in FIG. 7 (SEQ ID NO 24). Recombinant plasmids were screened by restriction digest and confirmed by sequencing. The resultant plasmid was named pAVE058. pAVE058 was transformed into *E. coli* W3110 to make CLD059, which was purified and maintained in glycerol stocks at −80° C.

The human erythropoietin (EPO) gene, which had been codon optimised for expression in *E coli*, was cloned as an Nde I/Xho I fragment into pAVE011 digested with Nde I and Xho I. The DNA sequence of the insert is shown in FIG. 8 (SEQ ID NO 25). Recombinant plasmids were screened by restriction digest and confirmed by sequencing. The resultant plasmid was named pAVE061. pAVE061 was transformed into *E. coli* W3110 to make CLD060, which was purified and maintained in glycerol stocks at −80° C.

Fed-batch fermentations using CLD054, CLD059 and CLD060 were carried out using the media and process conditions described in Example 11. Fermentations were maintained at 30° C. or 37° C. as described in Table 19. Fermentations were performed in batch mode until depletion of the carbon source (i.e. glycerol). Fed-batch fermentation was initiated at this point by the addition of a feed containing glycerol (714 g/L) and magnesium sulphate (30 g/L). Induction was carried out by addition of IPTG once the biomass level in the fermentation reached $OD_{600}$=50-60. The IPTG concentrations used are described in Table 17. The fed-batch phase was continued for 12-15 h post induction. Samples were taken throughout the fermentations to determine biomass level ($OD_{600}$) and protein product ((GST-3C, IFNα2 and EPO) titre (g/L), using Colloidal Blue stained SDS-PAGE gels of whole cell lysates of the sampled bacteria).

TABLE 17

| Strain | E. coli Host | Protein and Expression Vector Description | Ferm Temp ° C. | Induction IPTG Conc (mM) | OD600 | Product Titre (g/L) |
|---|---|---|---|---|---|---|
| CLD 054 | BL21 | GST-3C T7A3:DPPS91 | 37 | 0.50 | 100 | 8 |
| CLD 059 | W3110 | IFNα2 T7A3:DPPS91 | 37 | 0.10 | 120 | 9 |
|  |  |  | 37 | 0.25 | 150 | 14 |
|  |  |  | 37 | 0.50 | 160 | 14 |
| CLD 060 | W3110 | EPO T7A3:DPPS91 | 37 | 0.10 | 100 | >13 |
|  |  |  | 30 | 0.50 | 90 | >13 |

The data presented in Table 17 further demonstrate the utility of the systems for the manufacture of a wide range of heterologous proteins. High product titres are achieved using a simple generic fermentation process coupled with manipulation of only the concentration of IPTG used for induction. This is particularly beneficial to reduce the process development timelines for therapeutically useful heterologous proteins.

Example 17

The L-2-haloalkanoate dehalogenase (hadL) gene from *Pseudomonas putida* was cloned using Nde I and Spe I sites that had been engineered using PCR. The gene sequence is shown in FIG. 9 (SEQ ID NO 26). Plasmid pAVE011 was digested with Nde I and Spe I and the band was gel extracted. The hadL gene was digested with Nde I and Spe I and the hadL gene was gel extracted and ligated to pAVE011 to produce pAVE075. The *Pseudomonas savastanoi* origin of replication was copied using the PCR from Plasmid pCN60 (ATCC 77101; Nieto C, et al. (1990) Gene 87: 145-149).

The primers used were:

```
F37A: Sequence:
                                        (SEQ ID NO 27)
5' AGATCTACGCTTATGGGTGCCTTTCC,
and B29a: Sequence:
                                        (SEQ ID NO 28)
5' AGATCTAATACGCAAACCGCCTCTCC.
```

The PCR product was cloned initially into TOPO TA pCR2.1 (Invitrogen) and then into pAVE075 by Bgl II digestion. The resultant plasmid, pAVE086 was transformed into *Pseudomonas putida* NCIMB 12018, via electroporation to make CLD075, which was purified and maintained in glycerol stocks at −80° C. A vial of CLD075 was removed from a −80° C. freezer and allowed to thaw. 10 μl of the thawed glycerol stock was inoculated into 5 ml Luria Broth (LB, 5 g/L yeast extract (Oxoid), 10 g/L tryptone (Oxoid), and 5 g/L sodium chloride) supplemented with tetracycline (10 μg/ml). This was incubated at 30° C. in an orbital shaker for 16 h. 500 μl of this culture was then used to separately inoculate two 250 ml Erlenmeyer flasks containing 50 ml of Luria Broth (composition as described above). The flasks were incubated at 30° C., at 200 rpm in an orbital shaker. Growth was monitored until $OD_{600}$=0.5-0.7. At this point one flask was induced with IPTG to a final concentration 0.5 mM whilst the second flask was left un-induced to monitor basal expression. The incubation was continued, under the conditions described above, during which samples were taken for measurement of growth and accumulation of HadL protein within the bacterial cells. The accumulation level of HadL was determined using densitometry scanning of Colloidal Blue stained SDS-PAGE gels of whole cell lysates of the sampled bacteria.

Figure 10:
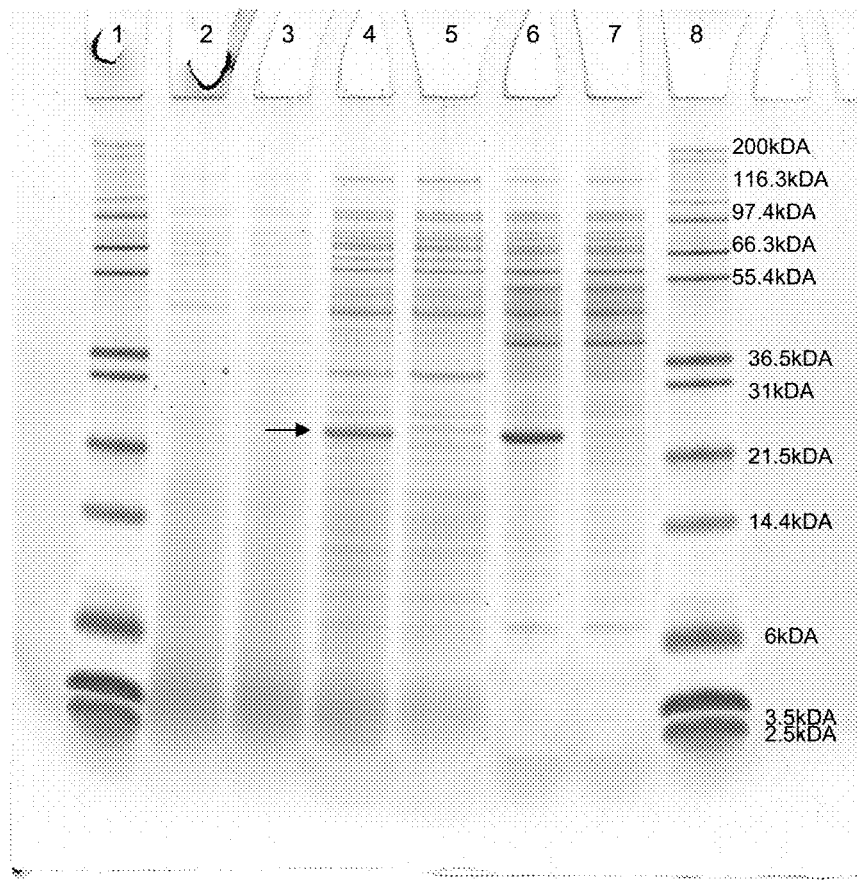
FIG. 10 shows the expression and accumulation of HadL protein according to Example 17.

The expression and accumulation of HadL protein is presented in FIG. 10. The data indicate that the T7A3: DPPS91 expression system functioned in another prokaryotic host system. Surprisingly, the expression system performed with the same efficiency in *Pseudomonas putida* as that observed when using *E. coli* as the host system. Basal expression was not detected even following 23 h incubation in the absence of inducer. High level protein expression and accumulation was achieved in *Pseudomonas putida* following induction using IPTG.

Example 18

Fed-batch fermentation using *Pseudomonas putida* CLD075 was carried out using the generic *E. coli* media and process conditions described in Example 11. Fermentations were maintained at 30° C. and pH 7.0 (controlled with 25% ammonium hydroxide and 10% phosphoric acid). Fermentations were performed in batch mode until depletion of the carbon source (i.e. glycerol). Fed-batch fermentation was initiated at this point by the addition of a feed containing glycerol (714 g/L) and magnesium sulphate (30 g/L). Induction was carried out by addition of 1 mM IPTG (final concentration) once the biomass level in the fermentation reached $OD_{600}$=50. The fed-batch phase was continued for 12-15 h post induction. Samples were taken throughout the fermentation to determine biomass level ($OD_{600}$) and HadL protein accumulation ((% TCP) Colloidal Blue stained SDS-PAGE gels of whole cell lysates of the sampled bacteria).

The growth of CLD075 and expression/accumulation of HadL protein following induction are presented in FIG. 11.

High levels of protein expression and accumulation (>40% TCP) were achieved using the expression system in *Pseudomonas putida* even by just using a generic growth medium designed for use with *E. coli*.

Example 19

A synthetic Gal repressor gene (*E. coli*) was cloned into vector pZen042 (as described in EP 0 502 637) as a PstI fragment into the PstI site. Clones were identified with the Gal repressor gene in both clockwise and anticlockwise orientations. A clone with anticlockwise orientation was selected to generate pAVE071.

Construction of the Gal promoter and operator sequences was initiated in plasmid pZT7#2.0, prepared as described in U.S. Pat. No. 6,537,779. pZT7#2.0 has a pAT153 vector backbone, cer stability sequence, tet A/R, a single native lac operator sequence upstream of the gene of interest and an upstream T4 transcription terminator. The native Gal operator sequence was modified to produce a perfect palindromic operator sequence. This was cloned into the plasmid described above using synthetic linkers by means of EcoRI and XbaI restriction enzyme sites. The linker GalB was prepared by annealing the oligonucleotides GalB1 and GalB2:

```
GalB1
                                        (SEQ ID NO 29)
5'AATTCATACCATAAGCCTAATTCTACGAATTATCAGAGTTCTGGTTAC
CGGTGTAAGCGCTTACACTGT

GalB2
                                        (SEQ ID NO 30)
5'CTAGACAGTGTAAGCGCTTACACCGGTAACCAGAACTCTGATAATTCG
TAGAATTAGGCTTATGGTATG
```

The linker was then ligated to plasmid pZT7#2.0 and transformed into cloning host strain XL-1 Blue MR (Stratagene) as an EcoR I/Xba I fragment. Initial screening of transformants was by restriction digestion using AgeI. The sequence was confirmed by sequencing. The hTNFα gene was cloned into this plasmid as a NdeI/XhoI fragment.

The hTNFα gene and partial Gal perfect palindromic operator sequence were cloned by digesting with XmaI and MscI and ligating into pAVE071 digested with XmnI and XmaI Clones were screened for the presence of the hTNFα gene by restriction digestion.

Upstream perfect palindromic Gal operator and Gal promotor were each cloned into this plasmid using synthetic linkers by means of StuI and EcoRI sites. Linker GalA was prepared by annealing the oligonucleotides GalA1 and GalA2:

```
GalA1
(SEQ ID NO 31):
5'CAATTGTGTAAGCGCTTACACAACTTTATTCCATGTCACACTTTTCG
CATCTTTGTTATGCTATGGTG

GalA2
                                        (SEQ ID NO 32)
5'AATTCACCATCGCATAACAAGGATGCGAAAAGTGTGACATGGAATAA
AGTTGTGTAAGCGCTTACACAATTG
```

The presence of the linker was detected with digestion with MfeI and confirmed by sequencing. This plasmid was transformed into *E. coli* strain W3110 to generate CLD085, which was purified and maintained in glycerol stocks at −80° C.

Figure 17:
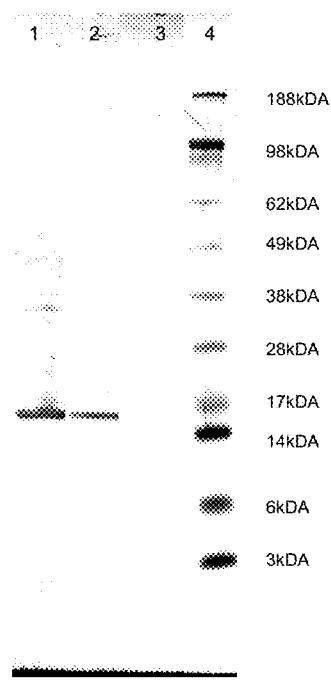
FIG. 17 shows the accumulation level of hTNF.

A vial of CLD085 was removed from the −80° C. freezer and allowed to thaw. 10 µl of the thawed glycerol stock was inoculated into 5 ml Luria Broth (LB, 5 g/L yeast extract (Oxoid), 10 g/L tryptone (Oxoid), and 5 g/L sodium chloride) supplemented with tetracycline (10 µg/ml). This was incubated at 37° C. in an orbital shaker for 16 h. 500 µl of this culture was then used to inoculate a 250 ml Erlenmeyer flask containing 50 ml of Luria Broth (composition as described above). The flask was incubated at 37° C., at 200 rpm in an orbital shaker. Growth was monitored until $OD_{600}$=0.5-0.7. At this point the flask was induced with galactose to a final concentration 10.0 mM. The incubation was continued, under the conditions described above, during which samples were taken for measurement of growth, accumulation of hTNFα within the bacterial cells. The accumulation level of hTNFα was determined using Western blot analysis (using anti-hTNFα antibody) following SDS-PAGE of the sampled bacteria. The data are presented in FIG. 17. This demonstrates that using perfectly palindromic gal operator sequences in combination with a gal repressor gene leads to very tight repression of the gal promoter in the absence of inducer whilst surprisingly still maintaining the capacity for induction when the inducer galactose is added.

Example 20

A non-integrating yeast vector was constructed as follows:

1) Clone Sequence 1 (*E. coli* Lac I downstream of a *Saccharomyces cerevisiae* CYC1 promoter) as a Xho I fragment into Xho I digested pCR2.1 (Invitrogen). Clone Sequence 1 is shown in FIG. 15 (SEQ ID NO 35).

2) Clone Sequence 2 (which consists of the *Saccharomyces cerevisiae* MF-α1 gene promoter with perfect palindromic lac operator sequences either side of the MF-α1 promoter region, with the gene sequence for the protein elafin with a C-terminal c-myc tag (elafin-cmyc) positioned downstream) as a Hind III fragment (made by PCR) into Hind III digested plasmid constructed in Step 1 to produce plasmid 2. Clone Sequence 2 is shown in FIG. 16 (SEQ ID NO 36).

3) Clone the Spe I fragment from YEp13 (ATCC37115), containing the LEU2 (selection marker gene) and the yeast 2µ origin of replication, into SpeI digested plasmid 2 to generate pAVE091.

pAVE091 plasmid DNA was transformed into *Saccharomyces cerevisiae* XS95-6C (ATCC 204688) by electroporation and positive colonies selected on yeast drop-out medium without leucine (Kaiser C, Michaelis S and Mitchel A (Methods in Yeast Genetics, Cold Spring Harbor Laboratory Manual, 1994)). Shake flask growth studies to determine elafin-cmyc protein expression were carried out using the same medium. The flasks were incubated at 30° C., at 200 rpm in an orbital shaker. The clones were grown to an OD of ~3 and induced with 0.5 mM IPTG (final concentration). The incubation was continued for a further 16 h, under the conditions described above, during which samples were taken for measurement of growth and secretion of elafin-cmyc protein into the growth medium. The secretion of elafin-cmyc into the residual growth medium was determined using an elastase inhibition enzyme assay, as described in Wiedow O, et al, J Biol Chem. (1990) 265(25): 14791-5. After 4 hours of IPTG induction there was 30 mg/L of active elafin protein in the growth medium. This demonstrates that the expression systems of the present invention are effective in yeasts.

Example 21

A DNA fragment was synthesised which contained the constitutive human Cytomegalovirus (hCMV) promoter flanked by dual perfect palindromic lac operator sequences. This was cloned into an expression vector, which expressed IgG Fc protein. The resulting plasmid was named pAVE081, and is derived from pCMV-Script (Stratagene) and contains the hCMV promoter flanked by dual perfect palindromic lac operator sequences on a Nde I/Nhe I fragment, with the IgG Fc DNA sequence in the multiple cloning site of the vector. The DNA sequence of the hCMV promoter and dual perfect palindromic lac operators is shown in FIG. 12 (SEQ ID NO 33). The DNA sequence of the IgG Fc protein is shown in FIG. 13 (SEQ ID NO 34). Transient co-transfections of pAVE081 expressing IgG Fc protein and pCMVlacI (Stratagene) which expresses lac repressor were carried out, as is well described in the art, to determine whether IgG Fc protein could be expressed under the control an IPTG inducible hCMV promoter-dual perfect palindromic lac operator expression system.

Figure 14:
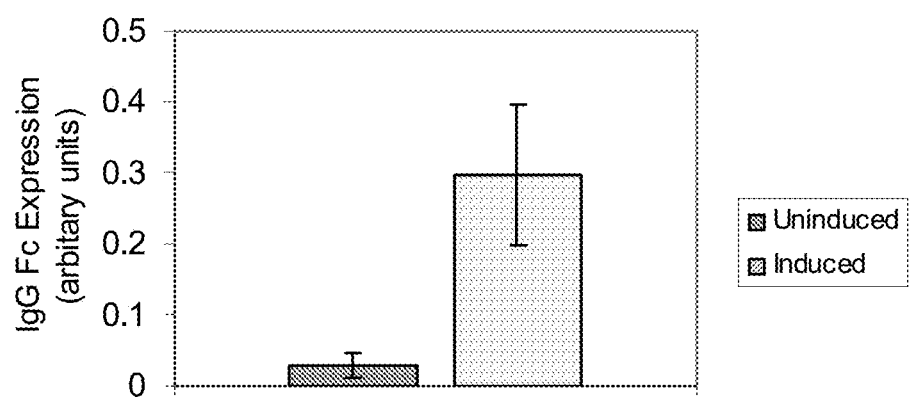
FIG. 14 shows the expression and secretion into the growth medium by the CHO cells of IgG Fc protein according to Example 21.

2 ml of Chinese Hamster Ovary (CHO cell line ECACC 85050302 adapted to suspension growth in serum free medium) suspension culture at $1.5 \times 10^5$ viable cells per ml was added to each well of 6-well tissue culture plates. The 6-well tissue culture plates were then incubated overnight (16 h) in a humidified 37° C. incubator with 5% $CO_2$ before transfection mixes were prepared containing 2 μg of pAVE081 DNA with an equal quantity of pCMVlacI (Stratagene) DNA, 6 μl of transfection reagent and 94 μl of growth medium per well. 100 μl of transfection mix was added to each well containing the CHO cells. The 6-well tissue culture plates were then incubated in humidified 37° C. incubator with 5% $CO_2$. To determine the level of expression/secretion of IgG Fc protein into the growth medium a set of wells (day 2) were induced with 5 mM IPTG (final concentration) and set of wells left un-induced. On day three the set of wells induced with IPTG and those left un-induced were sampled (post IPTG induction and un-induced). The expression and secretion into the growth medium by the CHO cells of IgG Fc protein was determined by ELISA as is well established in the art. The data obtained are shown in FIG. 14.

The data clearly demonstrates the broad utility of the expression system. The expression system can be used to control powerful constitutive promoters typically used with mammalian cell systems, such as the hCMV promoter, to express proteins in mammalian cells in a controllable, inducible manner.

The invention claimed is:

1. A perfect palindrome operator sequence-based recombinant protein expression system for expression of proteins in E. coli cells comprising an E. coli host cell comprising an expression cassette comprising:
   a) a λpL promoter;
   b) a single operator sequence, said operator sequence being a perfect palindrome operator sequence, wherein the operator sequence is located downstream of the promoter; and
   a sequence encoding a protein, the expression cassette further comprising a secretion signal sequence.

2. An expression system according to claim 1, wherein the perfect palindrome operator sequence overlaps the transcriptional start point.

3. A method for the production of a recombinant protein in an E. coli host cell which comprises the step of expressing the expression system according to claim 1 in the E. coli host cell.

4. A method according to claim 3, wherein the perfect palindrome operator sequence overlaps the transcriptional start point.

5. An E. coli host cell transformed with a plasmid, said plasmid comprising an expression cassette comprising:
   a) a λpL promoter;
   b) a single operator sequence, said operator sequence being a perfect palindrome operator sequence, wherein the operator sequence is located downstream of the promoter; and
   c) a sequence encoding a protein, the expression cassette further comprising a secretion signal sequence.

6. An E. coli host cell according to claim 5, wherein the perfect palindrome operator sequence overlaps the transcriptional start point.

7. A method for producing a protein, which comprises:
   a) culturing an E. coli host cell according to claim 5; and
   b) recovering the protein.

8. A method according to claim 7, wherein the perfect palindrome operator sequence overlaps the transcriptional start point.

9. A method according to claim 8, wherein the perfect palindrome operator sequence is a lac operator sequence.

* * * * *